United States Patent
Thompson et al.

(10) Patent No.: US 6,291,499 B1
(45) Date of Patent: Sep. 18, 2001

(54) 2-CYCLOHEXYL BENZIMIDAZOLE NMDA/NR2B ANTAGONISTS

(75) Inventors: Wayne Thompson, Lansdale; David A. Claremon, Maple Glen; Peter M. Munson, Harleysville; John A. McCauley, Maple Glen, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/696,612

(22) Filed: Oct. 25, 2000

Related U.S. Application Data

(60) Provisional application No. 60/162,714, filed on Oct. 29, 1999.

(51) Int. Cl.$^7$ .................. A61K 31/4184; C07D 235/04; A61P 25/28
(52) U.S. Cl. .................. 514/387; 548/304.4; 548/307.4; 548/309.4; 548/310.1; 548/331.1
(58) Field of Search .................. 514/387; 548/331.1, 548/304.4, 307.4, 309.4, 310.1

(56) References Cited

U.S. PATENT DOCUMENTS

| | | |
|---|---|---|
| 4,213,994 | 7/1980 | Gebert et al. . |
| 4,695,575 | 9/1987 | Janssens et al. . |
| 4,820,757 | 4/1989 | Spang et al. . |
| 5,306,723 | 4/1994 | Chenard . |
| 5,436,255 | 7/1995 | Butler . |
| 5,714,498 | 2/1998 | Kulagowski et al. . |
| 5,817,756 | 10/1998 | Kyle et al. . |
| 5,889,019 | 3/1999 | Mitch . |

FOREIGN PATENT DOCUMENTS

| | | |
|---|---|---|
| 0 441 506 B1 | 7/1994 | (EP) . |
| 0 787 493 A1 | 8/1997 | (EP) . |
| WO91/17156 | 11/1991 | (WO) . |
| WO92/19502 | 11/1992 | (WO) . |
| WO93/02052 | 2/1993 | (WO) . |
| WO94/29571 | 12/1994 | (WO) . |
| WO95/28057 | 10/1995 | (WO) . |
| WO96/37226 | 11/1996 | (WO) . |

OTHER PUBLICATIONS

J. D. Kristensen, et al., Pain, 51:249–253(1992).
K. Eida, et al., Pain ,61:221–228(1995).
D.J. Knox, et al., Anaesth. Intensive Care, 23:620–622(1995).
M. B. Max, et al., Clin Neuropharmacol., 18:360–368(1995).
I. Ishii, et al., J. Biol. Chem., 268:2836–2843(1993).
A. Wenzel, et al., Neuro Report, 7:45–48(1995).
D.J. Laurie, et al., Mol. Brain Res., 51:23–32(1997).
S. Boyce, et al., Neuropharmacology, 38:611–623(1999).
Z.-L. Zhou et al., J. Med. Chem., 42:2993–3000(1999).
T. F. Gregory, et al., Poster #94, 218th Nat'l Meeting Am. Chem. Soc., New Orleans, Louisiana, Aug. 22–26, 1999.
J. N. C. Kew, et al., Brit. J. Pharmacol., 123:463(1998).
J. J. Perkins et al., Tetrahedron Letts. 40:1103–1106(1999).
M. Povarny et al., Tetrahedron Lettrs 25:1322–1313(1994).

*Primary Examiner*—Deborah C. Lambkin
*Assistant Examiner*—Andrea M. D'Souza
(74) *Attorney, Agent, or Firm*—Shu Muk Lee; David L. Rose

(57) ABSTRACT

Novel 4-substituted cyclohexanes substituted in the 1-position with 2-benzimidazoles, 2-imidazopyridines, or 4-imidazoles either directly or through a $C_1$–$C_4$alkyl, cycloalkyl, hydroxyalkyl, alkoxy or aminoalkyl chain are effective as NMDA NR2B antagonists useful for relieving pain.

14 Claims, No Drawings

2-CYCLOHEXYL BENZIMIDAZOLE NMDA/NR2B ANTAGONISTS

This application claims benefit of 60/162,714 Oct. 29, 1999.

BACKGROUND OF THE INVENTION

Field of the Invention

This invention relates to novel 2-cyclohexyl benzimidazoles. In particular, this invention relates to novel 4-substituted cyclohexanes substituted in the 1-position with 2-benzimidazoles, 2-imidazopyridines, or 4-imidazoles either directly or through a $C_1-C_4$alkyl, cycloalkyl, hydroxyalkyl, alkoxy or aminoalkyl chain that are effective as NMDA NR2B antagonists useful for relieving pain.

Ions such as glutamate play a key role in processes related to chronic pain and pain-associated neurotoxicity—primarily by acting through N-methyl-D-aspartate ("NMDA") receptors. Thus, inhibition of such action—by employing ion channel antagonists, particularly NMDA antagonists—can be beneficial in the treatment and control of pain.

Known NMDA antagonists include ketamine, dextromorphan, and 3-(2-carboxypiperazin-4-yl)-propyl-1-phosphonic acid ("CPP"). Although these compounds have been reported (J. D. Kristensen, et al., *Pain,* 51:249–253 (1992); K. Eide, et al., *Pain,* 61:221–228 (1995); D. J. Knox, et al., *Anaesth. Intensive Care* 23:620–622 (1995); and M. B. Max, et al., *Clin. Neuropharmacol.* 18:360–368 (1995)) to produce symptomatic relief in a number of neuropathies including postherpetic neuralgia, central pain from spinal cord injury, and phantom limb pain, widespread use of these compounds is precluded by their undesirable side effects. Such side effects at analgesic doses include psychotomimetic effects such as dizziness, headache, hallucinations, dysphoria, and disturbances of cognitive and motor function. Additionally, more severe hallucinations, sedation, and ataxia are produced at doses only marginally higher than analgesic doses. Thus, it would be desirable to provide novel NMDA antagonists that are absent of undesirable side effects or that produce fewer and/or milder side effects.

NMDA receptors are heteromeric assemblies of subunits, of which two major subunit families designated NR1 and NR2 have been cloned. Without being bound by theory, it is generally believed that the various functional NMDA receptors in the mammalian central nervous system ("CNS") are only formed by combinations of NR1 and NR2 subunits, which respectively express glycine and glutamate recognition sites. The NR2 subunit family is in turn divided into four individual subunit types: NR2A, NR2B, NR2C, and NR2D. I. Ishii, et al., *J. Biol. Chem.,* 268:2836–2843 (1993), A. Wenel, et al., *Neural Report,* 7:45–48 (1995), and D. J. Laurie et al., *Mol. Brain Res.,* 51:23–32 (1997) describe how the various resulting combinations produce a variety of NMDA receptors differing in physiological and pharmacological properties such as ion gating properties, magnesium sensitivity, pharmacological profile, as well as in anatomical distribution.

For example, while NR1 is found throughout the brain, NR2 subunits are differentially distributed. In particular, it is believed that the distribution map for NR2B lowers the probability of side effects while producing pain relief. For example, S. Boyce, et al., *Neuropharmacology,* 38:611–623 (1999) describes the effect of selective NMDA NR2B antagonists on pain with reduced side-effects. Thus, it would be desirable to provide novel NMDA antagonists that target the NR2B receptor.

International Patent Publication WO94121615 describes benzimidazole-piperidine compounds utilized as dopamine D4 antagonists. Phenol compounds described as NMDA antagonists are described in U.S. Pat. Nos. 5,306,723 and 5,436,255, and in International Patent Publications WO91/17156, WO92/19502, WO93/02052, WO94/2957 1, WO95/28057, WO96/37226, and EP 04422506. Benzyl piperidines substituted with phenols or imidazoles are described in Z. -L. Zhou, et al., *J. Medicinal Chemistry,* 42:2993–3000 (1999); T. F. Gregory, et al., Poster #94, 218th National Meeting American Chemical Society, New Orleans, La., Aug. 22–26, 1999. Other NMDA NR2B selective compounds are described in European Patent Publication EP 787493 and *British J. Pharmacol.,* 123:463(1998). However, there continues to be a need for novel NMDA antagonists that target the NR2B receptor.

SUMMARY OF THE INVENTION

The present invention relates to novel 2-cyclohexyl benzimidazoles. The present invention also forms novel pharmaceutical compositions utilizing these novel compounds. Further, this invention includes novel methods to treat pain by utilizing the novel compounds.

DETAILED DESCRIPTION OF THE INVENTION

In one aspect, the compounds of this invention are represented by Formula (I):

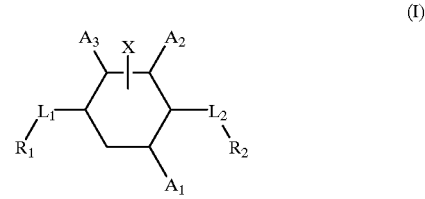

(I)

or pharmaceutically acceptable salts thereof, wherein $R_1$ is 2-benzimidazole, 2-imidazopyridine, or 2-quinazoline; optionally substituted with fluoro, amino, or hydroxy;

$R_2$ is phenyl, optionally substituted with one to five substituents, each substituent independently being chloro, fluoro, bromo, $C_1-C_4$alkyl, trifluoromethyl, hydroxy, or carboxy;

$L_1$ and $L_2$ are independently $C_1-C_4$alkyl, $C_1-C_4$alkenyl, $C_1-C_4$alkynyl, $C_1-C_4$alkoxy, amino, amino$C_1-C_4$alkyl, hydroxy$C_1-C_4$alkyl, carbonyl, cyclo$C_3-C_6$alkyl or aminocarbonyl;

$A_1$, $A_2$, and $A_3$ are each hydrogen or i) $A_1$ and $A_2$ form a two carbon bridge or ii) $A_1$ and $A_3$ form a two carbon bridge; and optionally substituted with X, wherein X is hydroxy, amino, $C_1-C_4$alkylamino, di($C_1-C_4$)alkylamino, $C_1-C_4$alkyl, ester, carbamate, carbonate, or ether.

In an embodiment, the compound of this invention is represented by Formula (I) or a pharmaceutically acceptable salt thereof, wherein $R_1$ is 2-benzimidazole;

$R_2$ is phenyl, optionally substituted with one to five substituents, each substituent independently being chloro, fluoro, bromo, $C_1-C_4$alkyl, trifluoromethyl, hydroxy, or carboxy;

$L_1$ and $L_2$ are independently $C_1$–$C_4$alkyl, $C_1$–$C_4$alkenyl, $C_1$–$C_4$alkynyl, $C_1$–$C_4$alkoxy, amino, amino$C_1$–$C_4$alkyl, hydroxy$C_1$–$C_4$alkyl, carbonyl, cyclo$C_3$–$C_6$alkyl or aminocarbonyl;

$A_1$, $A_2$, and $A_3$ are each hydrogen or i) $A_1$ and $A_2$ form a two carbon bridge or ii) $A_1$ and $A_3$ form a two carbon bridge; and optionally substituted with X, wherein X is hydroxy, amino, $C_1$–$C_4$alkylamino, di($C_1$–$C_4$)alkylamino, $C_1$–$C_4$alkyl, ester, carbamate, carbonate, or ether.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ling systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

Unless otherwise stated, the terms "carbonyl" and "aminocarbonyl" include short $C_1$–$C_2$ termini. The terms include, for example, —CO—, —CONH—, —$CH_2$CO—, —$CH_2$CONH—, —$C_2H_4$CO—, —$C_2H_4$CONH—, —CO$CH_2$—, —CONH$CH_2$—, —CO$C_2H_4$—, —CONH$C_2H_4$—, —$CH_2$COC$H_2$—, —$CH_2$CONH$CH_2$—, —$CH_2$CO$C_2H_4$—, —$CH_2$CONH$C_2H_4$—, —$C_2H_4$CO$C_2H_4$-, and —$C_2H_4$CONH$C_2H_4$—. Similarly, unless otherwise stated, the term "amino$C_1$–$C_4$alkyl" includes short $C_1$–$C_2$ termini. The term includes, for example, —$CH_2$NH—, —$C_2H_4$NH—, —$C_3H_6$NH—, —$C_4H_8$NH—, —$CH_2$NH$CH_2$—, —$C_2H_4$NH$CH_2$—, —$C_3H_6$NH$CH_2$—, —$C_4H_8$NH$CH_2$—, —$CH_2$NH$C_2H_4$—, —$C_2H_4$NH$C_2H_4$—, —$C_3H_6$NH$C_2H_4$—, —$C_4H_8$NH$C_2H_4$—, —NH$CH_2$—, —NH$C_2H_4$—, —NH$C_3H_6$—, —NH$C_4H_8$—, —$CH_2$NH$C_2H_4$—, —$CH_2$NH$C_3H_6$—, —$CH_2$NH$C_4H_8$—, —$C_2H_4$NH$C_3H_6$—, and —$C_2H_4$NH$C_4H_8$—.

Unless otherwise stated, the term "carbamate" is used to include —OCOO$C_1$–$C_4$alkyl, —NHCOO$C_1$–$C_4$alkyl, and —OCONH$C_1$–$C_4$alkyl.

The term "halogen" includes fluorine, chlorine, bromine and iodine atoms.

The term "SEM" is used to describe —$CH_2$—O—$CH_2CH_2$—Si($CH_3$)$_3$.

The term "$C_0$" means that the carbon is not present. Thus, "$C_0$–$C_5$" means that there are from none to five carbons present—that is, five, four, three, two, one, or no carbons present. Accordingly, "$C_0$–$C_5$alkyl" means a direct bond for the case of "$C_0$".

The term "optionally substituted" is intended to include both substituted and unsubstituted. Thus, for example, optionally substituted aryl could represent a pentafluorophenyl or a phenyl ring.

Compounds described herein contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 1 mg to about 500 mg of the active ingredient and each cachet or capsule preferably containing from about 1 to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula 1, or pharmaceutically acceptable salts thereof, may also be prepared in powder or liquid concentrate form.

Experimental Protocols

Assessing the Activity of Selected Compounds to Inhibit NR1A/2B NMDA Receptor Activation (FLIPR Assay)

The activity of selected compounds to inhibit NR1A/2B NMDA receptor activation measured as NR1A/2B receptor-mediated $Ca^{2+}$ influx is assessed by the following procedure:

NR1A/2B receptor transfected L(tk) cells are plated in 96-well format fat 3×10 cells per plate and grown for one–two days in normal growth media (Dulbeccos MEM with Na pyruvate, 4500 mgglucose, pen/strep, glutamine, 10% FCS and 0.5 mg/ml geneticin). NR1A/2B-expression in these cells is induced by the addition of 4 nM dexamethasone in the presence of 500 μM ketamine for 16–24 hours. After receptor induction cells are washed using a Labsystem Cellwasher two times with assay buffer (Hanks balanced salt solution (HBSS-Mg++ free) containing 20 mM HEPES, 0.1% BSA, 2 mM $CaCl_2$ and 250 μM probenecid). The cells of each 96 well cell plate are loaded with the Ca sensitive dye Fluo-3 (Molecular Probes, Inc.) at 4μM in assay buffer containing 0.5% FBS, and 0.04% pluronic F-127 (Molecular Probes, Inc.) for 1h at 37° C. avoiding light. The cells are then washed with the Cellwasher four times with assay buffer leaving them in 100 μl buffer. Test compounds in solution are pipetted by FLIPR (Fluorometric Imaging Plate Reader) into each test well for a 2 min pretreatment. During this time the fluorescence intensity is recorded (excitation at 488 nm and emission at 530 nm). The glutamate/glycine 50 μl agonist solution (final concentration 1 μM/1 μM) is then added by FLIPR into each well already containing 150 μl of buffer (containing the test compound or vehicle) and the fluorescence is continuously monitored for 10 min. The endpoint fluorescence values are used to determine an $IC_{50}$ value comparing the agonist-stimulated signal for the vehicle alone sample and that for the cells incubated with each concentration of test compound.

Determining the Apparent Dissociation Constant (Ki) of Compounds for Human NR1A/NR2B Receptors (Binding Assay):

The radioligand binding assay is performed at room temperature in 96-well microtiter plates with a final assay volume of 1.0 mL in 20 mM Hepes buffer (pH 7.4) containing 150 mM NaCl. Solutions of test compounds were prepared in DMSO and serially diluted with DMSO to yield 20 μL of each of 10 solutions differing by 3-fold in concentration. Non-specific binding (NSB) using hot AMD-1 (10 μM final concentration) and total binding (TB) by using DMSO (2% final concentration). A solution of NR1A/NR2B receptors (40 μM final concentration) and tritiated AMD-2 (1 nM final concentration) were added to the test compounds. After 3 h of incubation at room temperature, samples are filtered through Packard GF/B filters (presoaked in 0.05% PEI, polyethyleninine Sigma P-3143) and washed 10 times with 1 mL of cold 20 mM Hepes buffer per wash. After vacuum drying of the filter plates, 40 μL of Packard Microscint-20 was added and bound radioactivity determined in a Packard TopCount. The apparent dissociation constant (Ki), the maximum percentage inhibition (%$I_{max}$), the minimum percentage inhibition (%$I_{min}$) and the hill slope (nH) were determined by a non-linear least squares fitting the bound CPM data to Equation #1 below. Equation#1:

$$CPM\ Bound = \frac{(SB)(\%\ I_{max} - \%\ I_{min})}{(1+([Drug]/(Ki[L-844,345]/K_D))^{nH})} + NSB + (SB)(1-\%\ I_{max})$$

where, $K_D$ is the apparent dissociation constant for the radioligand for the receptor as determined by hot saturation and SB is the specifically bound CPM determined from the difference of TB and NSB.

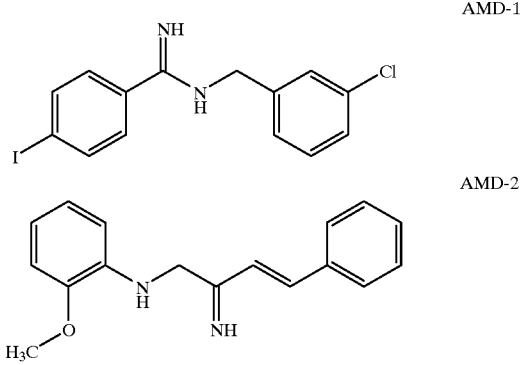

Compounds AMD-1 and AMD-2 can be synthesized in accordance with the following general reaction schemes.

SCHEME 1

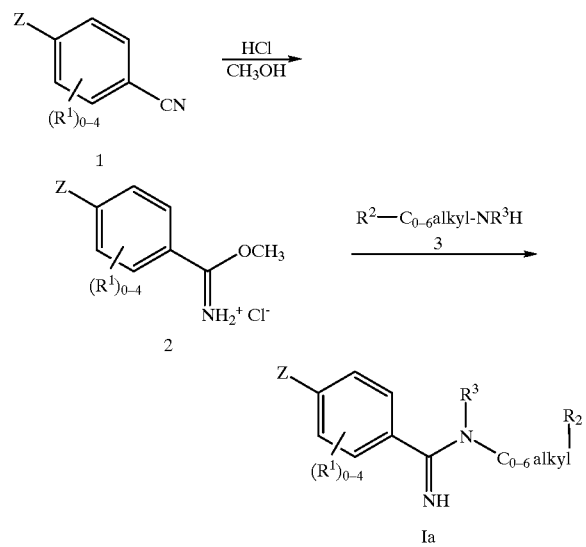

In accordance with scheme 1, hydrogen chloride is bubbled through a solution of the appropriately substituted benzonitrile 1 in methanol at room temperature. The volatiles are removed under reduced pressure and the resulting residue is triturated with ether and filtered to yield the desired imidate 2. Imidate 2 is dissolved in methanol at ambient temperature, treated with amine 3 at ambient temperature and stirred under argon. The volatiles are removed under reduced pressure and the residue purified by preparative HPLC or trituration with ether to afford amidine Ia.

SCHEME 2

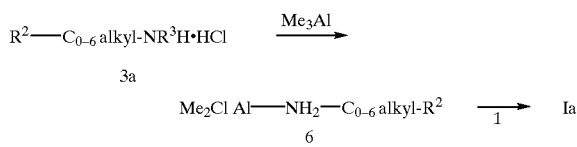

In accordance with scheme 2, at room temperature under argon, amine 3a is dissolved in ether and was treated with 1-M hydrogen chloride in ether (1 equiv.) in a single portion. The resulting precipitate is stirred vigorously for 10 minutes.

The volatiles are removed under reduced pressure. The residue is suspended in toluene, cooled to 0° C. under argon, treated with 2.0-M trimethylaluminum (1.05 equiv.) in a dropwise manner, and stirred for 45 minutes at room temperature to afford intermediate 6 (not isolated). Compound 6 is added to a solution of nitrile 1 in toluene. The reaction is heated to 80° C. without stirring in a sealed tube for 18 h, cooled to ambient temperature, poured onto a silica gel column and eluted with methanol/dichloromethane to give the amidine 4.

Preparation of [$^{125}$I]AMD-1

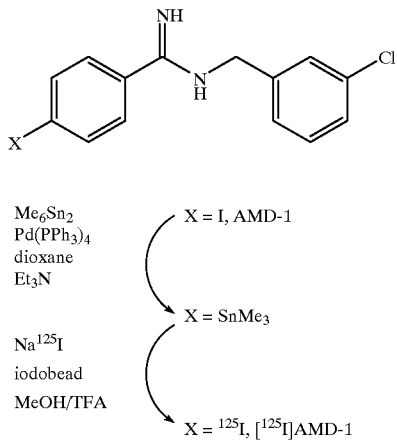

Tritiated AMD-1 was prepared by the following procedure: A mixture of AMD-1, hydrochloride salt, (5 mg, 0.012 mmol) in dioxane (0.2 mL) containing triethylamine (4 μL) was treated with hexamethylditin (5 μL), a catalytic amount of palladium catalyst and heated at 100° C. for 45 minutes. The reaction was cooled to room temperature, filtered through a glass wool plug, rinsed with methanol and concentrated in vacuo to give 10.7 mg of a brown oil. The oil was dissolved in methylene chloride and passed through a small silica column eluting with methylene chloride followed by 5% methanol/methylene chloride. Fractions containing the trimethylstannane (Rf 0.26 in 10% methanol/methylene chloride) were pooled and concentrated in vacuo to give 4.5 mg of the trimethylstannane as a clear colorless oil. This material was further purified by HPLC (C18 Econosil, 10×250 mm, 20 minute linear gradient, 30% MeCN:70% H$_2$O (0.1% TFA) to 90% MeCN, 3mL/min, 254 nm, retention time 15 minutes) to give 3 mg of the trimethylstannane.

A Na$^{125}$I shipping vial (10 mCi, Amersham) was charged with a stir bar, an iodobead, 50 μL of methanol and stirred five minutes at room temperature. A solution of the trimethylstannane (0.1 mg) in 50 μL of methanol containing 5 μL of trifluoroacetic acid was added and the reaction was stirred for five minutes. The reaction was quenched with 50 μL of ammonium hydroxide and purified by HPLC (C18 Vydac protein and peptide column, 4.6×250 mm, 20 minute linear gradient, 30% MeCN:70% H$_2$0 (0.1% TFA) to 90% MeCN, 1 ml/min, retention time 11 minutes). Fractions containing the radioactive product were pooled and concentrated in vacuo to give 989 μCi of [$^{125}$I]AMD-1 with a specific activity of 898Ci/mmol as measured by UV absorbance at 272 nm.

Synthesis of Tritiated AMD-2

Tritiated AMD-2 was prepared by the following procedure: The phenol of AMD-2 (2 mg, 0.008 mmol) dissolved in dimethylformamide (0.6 mL) and potassium carbonate (1.2 mg) for 1 hr. High specific activity tritiated methyl iodide (50 mCi, 0.0006 mmol, in toluene 1 mL, American Radio-labeled Chemicals) was added at room temperature and stirred for 2 hours. The reaction mixture was filtered using a Whatman PTFE 0.45 μm syringeless filter device to remove any insoluable potassium carbonate, washed with Abs. ethanol (2 mL, Pharmco), and the combined filtrates were concentrated to dryness at room temperature using a rotary evaporator; this also removed any unreacted tritiated methyl iodide. The residue was purified by HPLC chromatography on a Phenomenx Luna C8 semi-prep column (Luna 5 micro C8(2), 250×10.0 mm) using a gradient system of 20/80 acetonitrile/water with 0.1% trifluoroacetic acid to 100% acetonitrile with 0.1% trifluoroacetic acid in 20 min. Total activity of the product was 8 mCi. Further purification was effected by absorption onto a Waters C-18 Sep-pak column (Waters Sep-Pak PLUS C18) and elution with water followed by absolute ethanol. The product was diluted with absolute ethanol (10 mL) before submission for final analysis.

The compounds of this invention exhibit less than 50 μM in the FLIBR and binding assays. Thus, the compounds and pharmaceutical compositions of this invention have been found to exhibit biological activity as NMDA NR2B antagonists. Accordingly, another aspect of the invention is the treatment of pain, migraine, depression, anxiety, schizophrenia, Parkinson's disease, or stroke—maladies that are amenable to amelioration through inhibition of NMDA NR2B receptors—by the administration of an effective amount of the compounds of this invention.

The following examples are provided to more fully illustrate the present invention, and are not to be construed as limiting the scope of the claims in any manner.

EXAMPLES

The compounds of this invention can be prepared according to Scheme 1 shown below:

Scheme 1

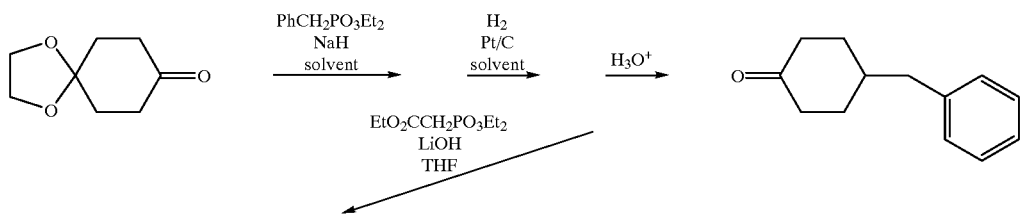

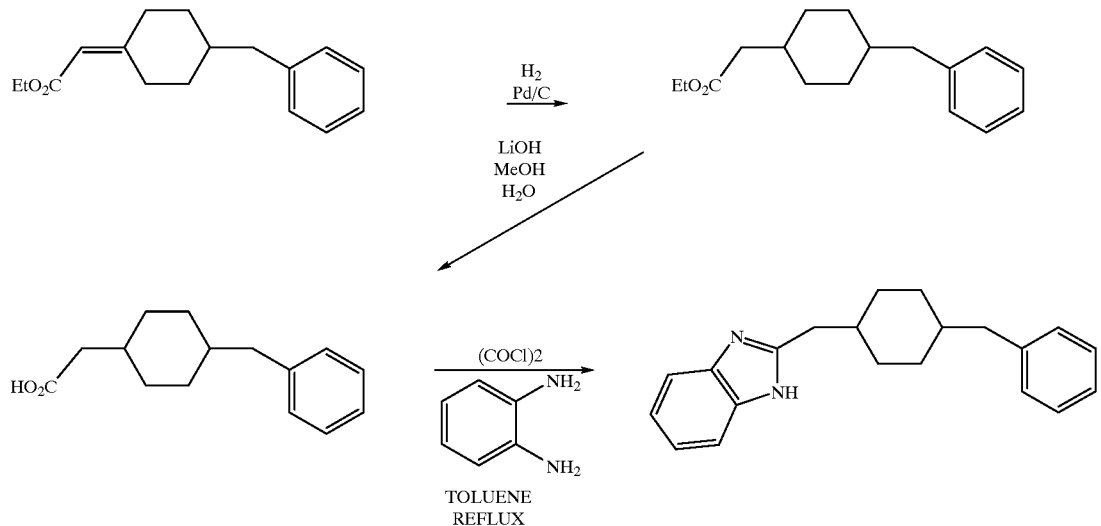
The compounds of this invention can be prepared according to Scheme 2 shown below:
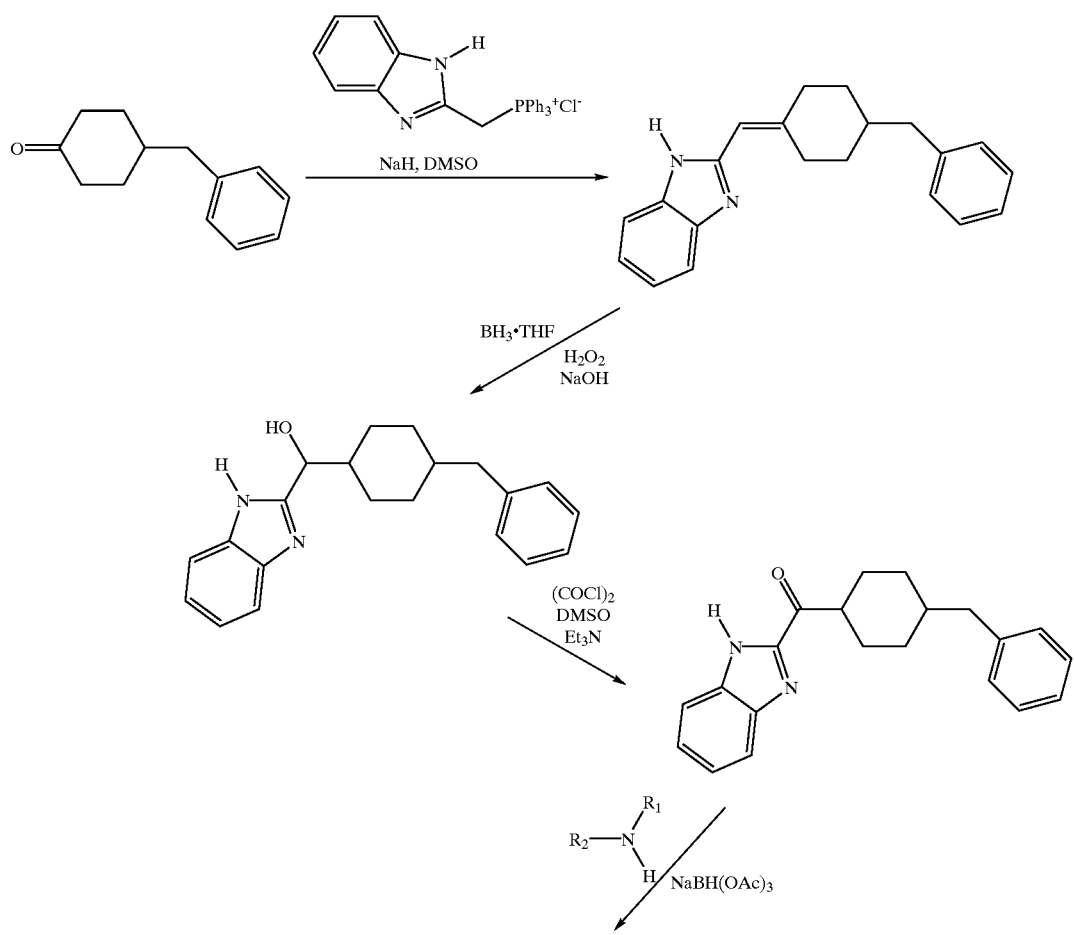

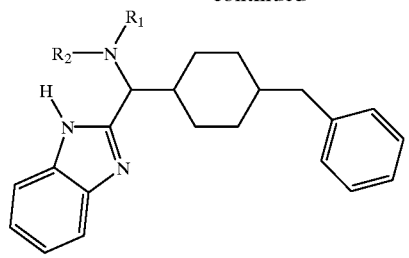
The compounds of this invention can be prepared according to Scheme 3 shown below:
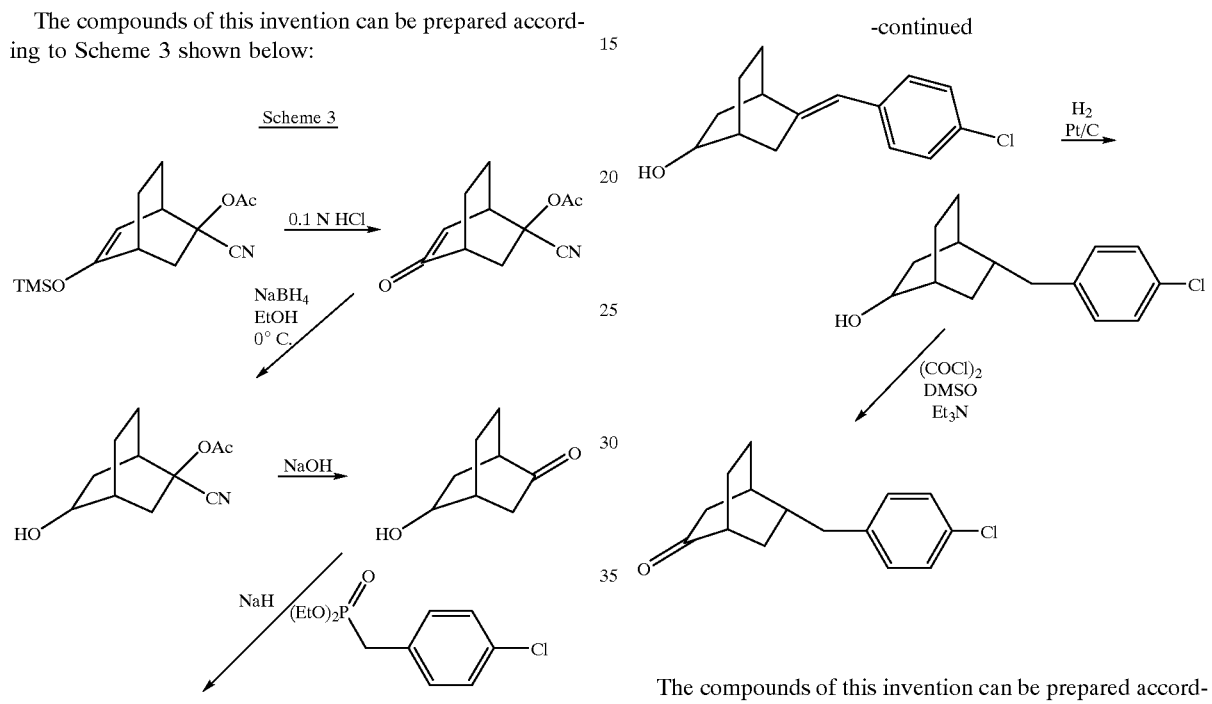
The compounds of this invention can be prepared according to Scheme 4 shown below:
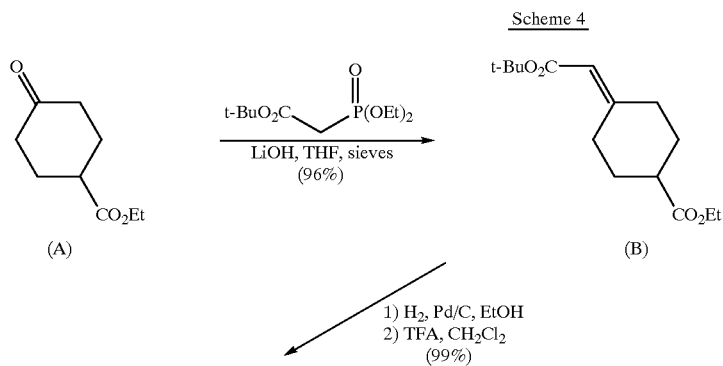

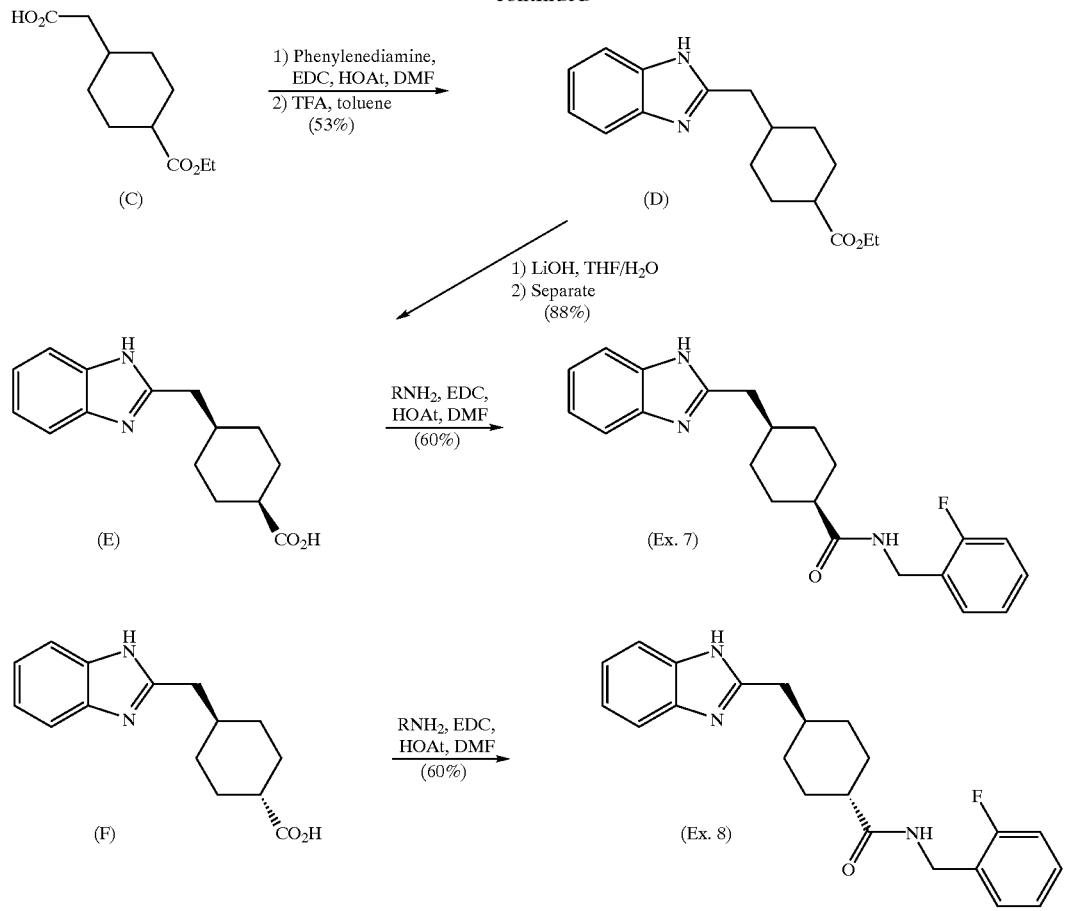
The compounds of this invention can be prepared according to Scheme 5 shown below:
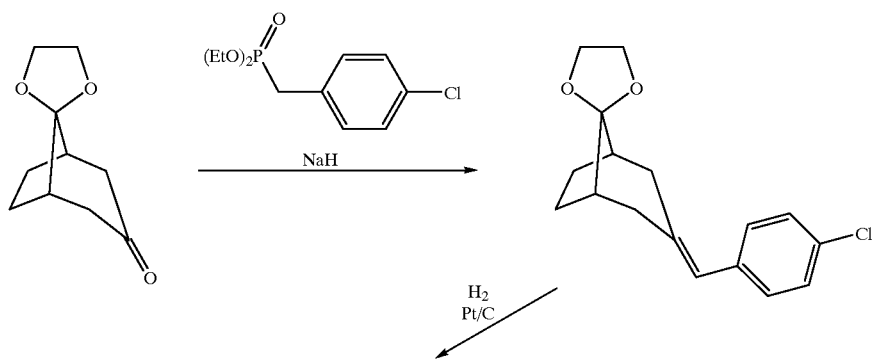
Scheme 5

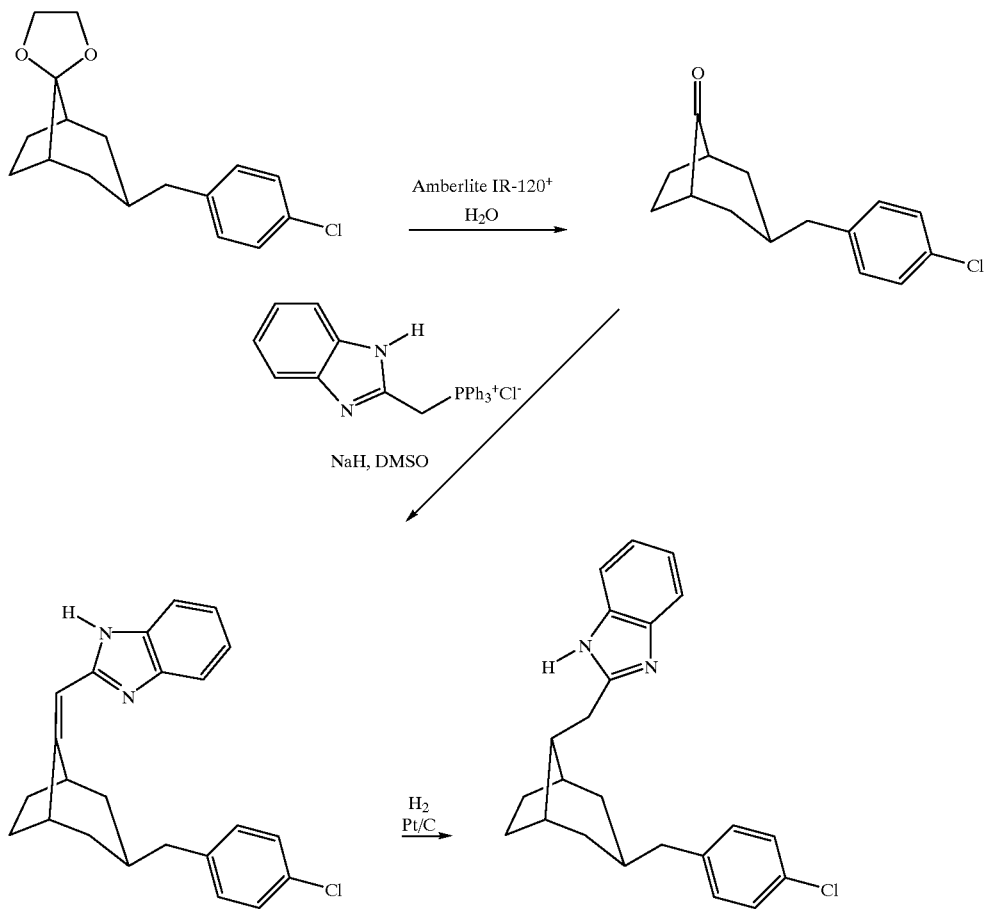
The compounds of this invention can be prepared according to Scheme 6 shown below:
Scheme 6
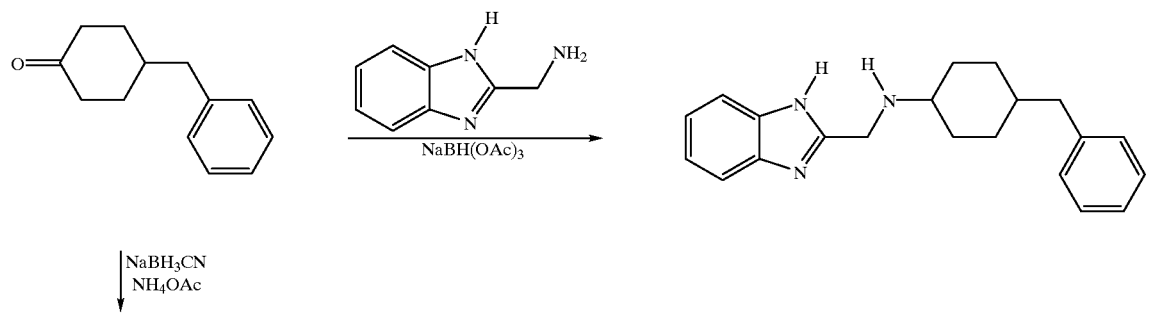

-continued

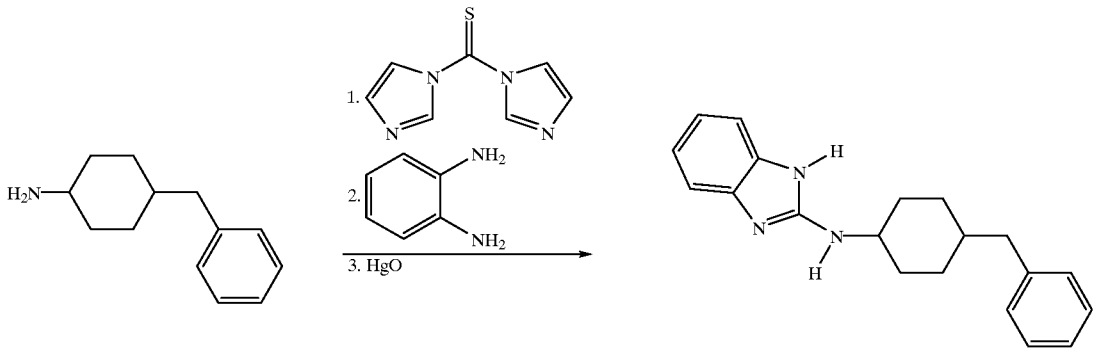

Example 1

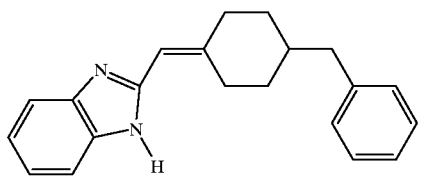

2-(4-Benzyl-cyclohexylidenemethyl)-1H-benzimidazole

Example 1 was prepared by the following procedure.

Step 1:

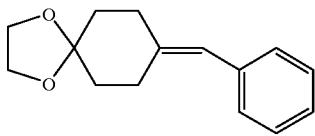

8-Benzylidene-1,4-dioxa-spiro[4.5]decane:

To a stirred solution of 20 g of 1,4-dioxa-spiro[4.5]decan-8-one and 35 g of diethyl benzylphosphonate in 60 mL of 1,3-dimethyl-2-imidazolidinone dried over 4 Å mol sieves was added 7 g of 60% NaH oil dispersion. The mixture was allowed to stir overnight, diluted with 500 mL of water and extracted with 3×100 mL of ether. Combined extracts were dried over magnesium sulfate and concentrated under reduced pressure. Chromatography over silica gel eluting with a gradient of 5:95 ethyl acetate:hexane to 1:3 ethyl acetate:hexane gave 28 g of olefin as a colorless oil.

Step 2:

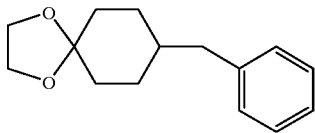

8-Benzyl-1,4-dioxa-spiro[4.5]decane:

A solution of 28 g of 8-benzylidene-1,4-dioxa-spiro[4.5] decane and 1 g of 5% palladium on carbon in 250 mL of ethanol was allowed to stir overnight under 1 atm of hydrogen The catalyst was filtered off and the solution concentrated to give 28 g of 8-benzyl-1,4-dioxa-spiro[4.5] decane as an oil.

Step 3:

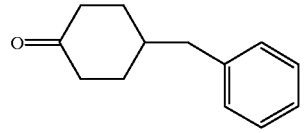

4-Benzyl-cyclohexanone:

A mixture of 28 g of 8-benzyl-1,4-dioxa-spiro[4.5] decane, 100 mL of water, 10 mL of methanol and 20 g of Amberlite™ IR-120+ was heated to reflux for 5 h. After cooling, removal of solvents under reduced pressure gave 24 g of 4-benzyl-cyclohexanone as an oil.

Step 5:

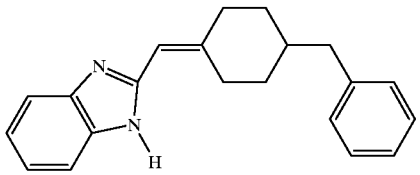

2-(4-Benzyl-cyclohexylidenemethyl)-1H-benzimidazole:

A stirred solution of 0.5 g of 4-benzyl-cyclohexanone, 1.0 g of 2-benzimidazolylmethyltriphenylphosphonium chloride and 15 mL of anhydrous DMSO was heated gently until a clear solution was obtained, then cooled to room temperature. To this solution was added 90 mg of 60% sodium hydride oil dispersion. The resulting orange solution was stirred for 48 h at room temperature, then quenched with 200 mL of water and extracted into 3×50 mL portions of ethyl acetate. The combined extracts were dried over magnesium sulfate and concentrated. Purification by preparative TLC eluting with 25% ethyl acetate in hexane gave 220 mg of a white solid: MS (m+1)=303.4; $^1$H NMR (400 MHz, CDCl$_3$) 7.5 (m, 2H), 7.2–7.0 (3×m, 7H), 6.2 (s, 1H), 3.75 (d, 1H), 2.45 (dd, 2H), 2.3 (d, 1H), 2.2 (t, 1H), 2.05 (m, 1H), 1.8 (m, 4H), 1.05 (m, 2H).

Example 2

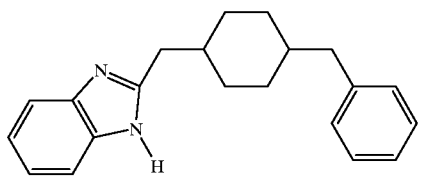

2-(4-Benzyl-cyclohexylmethyl)-1H-benzimidazole:

Hydrogenation of 0.10 g of 2-(4benzyl-cyclohexylidenemethyl)-1H-benzimidazole over 0.05 g of 5% platinum on carbon in 10 mL of ethanol at 1 atm overnight gave 0.1 g of 2-(4-benzyl-cyclohexylmethyl)-1H-benoimidazole as a 2:1 mixture of cis and trans isomers. Chromatography on a Chiralpak™ column eluting with a gradient of 70:30 to 30:70 hexane and 2-propanol gave 2-(4-benzyl-cyclohexylmethyl)-1H-benoimidazole: RT=??????min; MS (m+1)=; $^1$H NMR (400 MHz, CDCl$_3$)

Later fractions yielded 2-(4-benzyl-cyclohexylmethyl)-1H-benoimidazole; MS (m+1) =; $^1$H NMR (400 MHz, CDCl$_3$)

Example 3

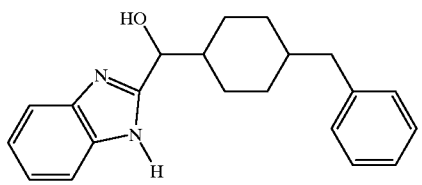

(1H-Benzoimidazol-2-yl)-(4-benzyl-cyclohexyl)-methanol:

Example 3 was prepared by the following procedure. To a stirred solution of 20 mg of 2-(4benzyl-cyclohexylidenemethyl)-1H-benzimidazole in 10 mL of THF cooled in an ice bath was added 1 mL of 1M borane•THF. After stirring for 24 h warming to room temperature, 0.5 mL of water was added followed by 0.5 mL of 6N sodium hydroxide and 0.5 mL of 30% hydrogen peroxide. After 30 min, the solution was diluted with 100 mL of chloroform, washed 2×10 mL of water, dried over magnesium sulfate and concentrated to dryness.

Preparative thin-layer chromatography eluting with 25%ethyl acetate in hexane gave 11 mg of (±)-cis and trans (1H-benzimidazol-2-yl)-(4-benzyl-cyclohexyl)-methanol as a gummy resin: MS (m+1)=321.4; $^1$H NMR (400 MHz, CDCl$_3$) 7.6 (m, 2H), 7.2 (m, 7H), 4.85 and 4.8 (2×d, 1H), 2.6 and 2.42 (2×d, 2H).

Example 4

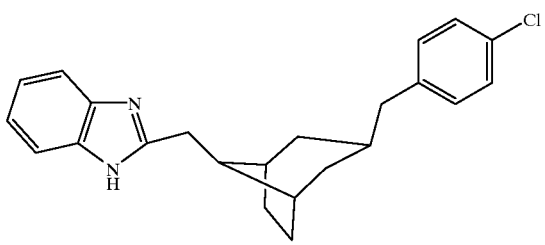

2-[3-(4-Chloro-benzyl)-bicyclo[3.2.1]oct-8-ylmethyl]-1H-benzimidazole

Example 4 was prepared by the following procedure.

Step 1:

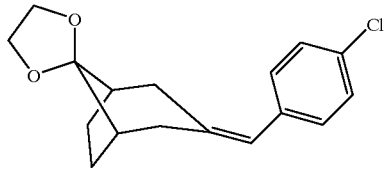

Ethylene ketal of 3-(4-chloro-benzylidene)-bicyclo[3.2.1]octan-8-one:

To a stirred solution of 1 g of 3-mono-ethylene ketal of bicyclo[3.2.1]octane-3,8-dione (prepared by Jones oxidation of the mono-ethylene ketal of 3-endo-hydroxy-bicyclo[3.2.1]octan-8-one which was prepared by the procedure described by M. Povarny, P. Schreiber, G. Kraiss and K. Nador, *Tetrahedron Letters*, 25:1311–12(1984) and 2.4 g of diethyl 4-chlorobenzylphosphonate in 5 mL of 1,3-dimethyl-2-imidazolidinone dried over 4 Å mol sieves was added 0.30 g of 60% NaH oil dispersion. The mixture was allowed to stir overnight, diluted with 200 mL of water and extracted with 3×100 mL of ethyl acetate. Combined extracts were dried over magnesium sulfate and concentrated under reduced pressure. Low pressure chromatography over silica gel eluting with a gradient of 5:95 ethyl acetate:hexane to 1:3 ethyl acetate:hexane gave 1.9 g of the ethylene ketal of 3-(4chloro-benzylidene)-bicyclo[3.2.1]octan-8-one as a colorless oil.

Step 2:

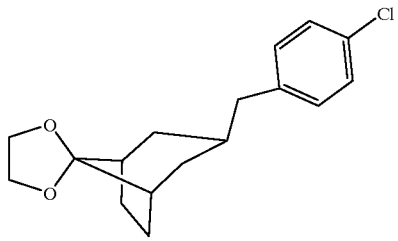

Ethylene ketal of 3-(4-chloro-benzyl)-biyclo[3.2.1]octan-8-one:

Hydrogenation of 1.9 g of the ethylene ketal of 3-(4chloro-benzylidene)-bicyclo[3.2.1)octan-8-one over 0.4 g of 5% platinum on carbon in 50 mL of ethans under 1 atm of hydrogen for 3 h gave 1.9 g the ethylene ketal of 3-(4chloro-benzyl)-bicyclo[3.2.1]octans-8-one as a thick oil: $^1$H NMR (400 MHz, CDCl$_3$): The crude product was a 3:1 mixture of exo:endo by peak integration of the exo benzylic protons at 2.45 (d):endo benzylic protons at 2.78 (d).

Step 3:

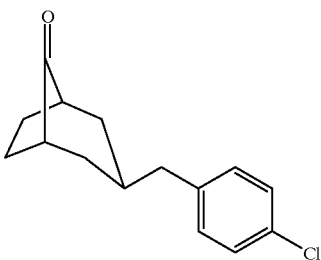

3-(4-Chloro-benzyl)-bicyclo[3.2.1]octan-8-one:

A stirred mixture of 1.9 g of the ethylene ketal of 3-(4-chloro-benzyl)-bicylo[3.2.1]octan-8-one, 10 mL of dioxane, 50 mL of water and 5 g of Amberlite™ IR-120+ was heated to Teflux for 8 h, cooled, filtered and extracted into 5×50 mL of ether. Combined extracts were dried over magnesium sulfate and concentrated. The crude 3:1 mixture of exo and endo 3-(4-chloro-benzyl)-bicyclo[3.2.1]octan-8-one, 1.3 g, was an oil.

Step 4:

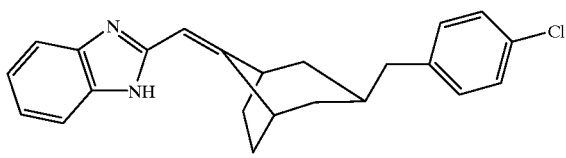

2-[3-(4-Chloro-benzyl)-bicyclo[3.2.1]oct-8-ylidenemethyl]-1H-benzimidazole:

To a stirred solution of 0.25 g of 2-benzimidazolylmethyl triphenyl phosphonium chloride and 0.1 g of 3-(4-chloro-benzyl)-bicyclo[3.2.1]octan-8-one in 5 mL of DMSO (heat to dissolve) at room temperature was added 60 mg of sodium hydride 60% oil dispersion. After the orange-red mixture was stirred for 24 h, conversion was complete and the solution was diluted with 100 mL of water and extracted into 3×25 mL of ethyl acetate. Combined extracts were dried over magnesium sulfate and concentrated. Purification by chromatography, eluting with 50% ethyl acetate in hexane gave 40 mg of 2-[3-(4chloro-benzyl)-bicyclo[3.2.1]oct-8-ylidenemethyl]-1H-benzimidazole.

Step 5:

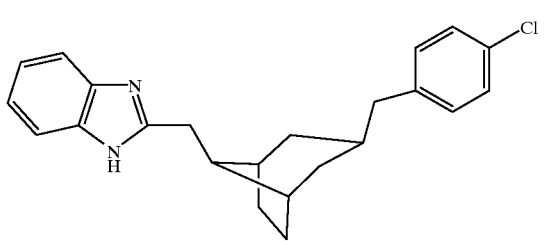

2-[3-exo-(4-Chloro-benzyl)-bicydo[3.2.1]oct-8-yl-exo-methyl]-1H-benzimidazole:

Hydrogenation of 40 mg of the ethylene ketal of 3-(4-chloro-benzylidene)-bicyclo[3.2.1]octan-8-one over 0.05 g of 5% platinum on carbon in 10 mL of ethanol under 1 atm of hydrogen for 3 h gave 40 mg of 2-[3-(4-chloro-benzyl)-bicyclo[3.2.2]oct-8-ylmethyl-1H-benzimidazole as a mixture of 3-exo-8-exo and 3-exo-8-endo isomers. Preparative TLC eluting with 50% ethyl acetate in hexane gave two bands. The major upper band was the 3-exo-8-exo 2-[3-(4-chloro-benzyl)-bicyclo[3.2.1]oct-8-ylmethyl]-1H-benzimidazole: $^1$H NMR (m+1)=321.4; $^1$H NMR (400 MHz, CDCl$_3$) 7.6 (m, 2H), 7.2 (m, 7H), 4.85 and 4.8 (2×d, 1H), 2.6 and 2.42 (2×d, 2H).

Example 5

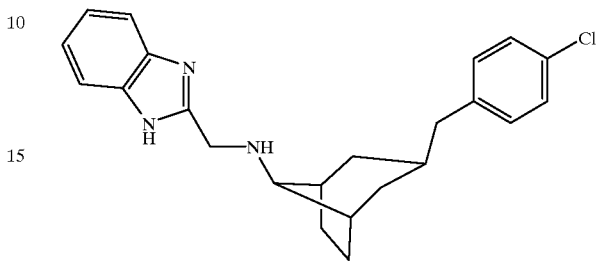

(1H-Benzimidazol-2-ylmethyl)-[3-(4-chloro-benzyl)-bicyclo[3.2.1]oct-8-yl]-amine:

A mixture of 250 mg of 3:1 mixture of exo and endo 3-(4-chloro-benzyl)-bicyclo[3.2.1]octan-8-one, 400 mg of 2-aminomethylbenzimidazole dihydrochloride, 150 mg of anhydrous sodium acetate, 10 mL of 1,2-dichloroethane and 400 mg of sodium triacetoxyborohydride was stirred overnight in a stoppered flask. The mixture was diluted with 50 mL of chloroform and washed with 20 mL of saturated sodium carbonate. The organic extract was dried over magnesium sulfate and concentrated under reduced pressure. Preparative TLC eluting with 225:25:5 chloroform:methanol:concentrated ammonium hydroxide gave in the fastest band the product as a mixture of two isomers. Crystallization and preparative TLC with 75:25:10 tetrahydrofuran:hexane:triethylamine or chromatography on Chiralpak™ AD eluting with 90:10 0.1% diethylamine in hexane:ethanol gave 150 mg of pure 3-exo-8-exo (1H-benzimidazol-2-ylmethyl)-[3-(4chlorobenzyl)-bicyclo[3.2.1]oct-8-yl]-amine: RT=5.8 min; MS (m+1)=380.9; $^1$H NMR (400 MHz, CDCl$_3$) 9.5 (br, 1H), 7.7 (br, 1H), 7.5 (br, 1H), 7.2 (m, 4H), 7.1 (d, 2H), 4.1 (s, 2H), 2.8 (m, 1H), 2.5 (d, 2H), 2.1 (s, 2H), 2–1.2 (complex, 11H).

Later fractions gave 50 mg of pure 3-endo-8-exo (1H-benzimidazol-2-ylmethyl)-[3-(4-chloro-benzyl)-bicyclo[3.2.1]oct-8-yl]-amine: RT =9 min; MS (m+1)=380.9; $^1$H NMR (400 MHz, CDCl$_3$) 9.5 (br, 1H), 7.7 (br, 1H), 7.5 (br, 1H), 7.2 (m, 4H), 7.1 (d, 2H), 4.18 (s, 2H), 2.82 (m, 1H), 2.78 (d, 2H), 2.06 (s, 2H), 2.1–1.2 (complex, 11H).

Example 6

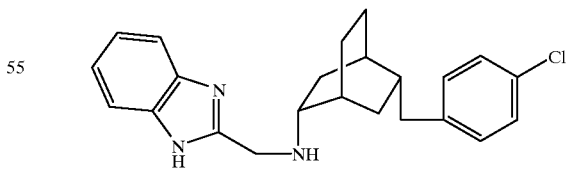

(1H-Benzimidazol-2-ylmethyl)-15-(4-chloro-benzyl)-bicyclo[2.2.2]oct-2-yl]-amine:

Example 6 was prepared in a similar manner to Examples 4 and 5 above. A mixture of 250 mg of 3:1 mixture of exo and endo 5-(4-chloro-benzyl)-bicyclo[2.2.2]octan-2-one was prepared from 5-acetoxy-5-cyanobicyclo[2.2.2]octan-2-one in three sequential steps without isolating intermediate products. The first two steps were similar to those described in Steps 1 and 2 of Example 4 above, sequential treatment with sodium borohydride in ethanol, sodium hydroxide, formed 5-hydroxybicyclo[2.2.2]octan-2-one. Olefination, hydrogenation, and Swern oxidation of the product, 5-(4-chloro-benzyl)-bicyclo[2.2.2]octan-2-ol followed. To the resulting product was added 400 mg of 2-aminomethylbenzimidazole dihydrochloride, 150 mg of anhydrous sodium acetate, 10 mL of 1,2-dichloroethane and 400 mg of sodium triacetoxyborohydride, and stirred overnight in a stoppered flask. The mixture was diluted with 50 mL of chloroform and washed with 20 mL of saturated sodium carbonate. The organic extract was dried over magnesium sulfate and concentrated under reduced pressure. Preparative TLC eluting with 95:5:5 ethyl acetate:methanol:triethyl amine gave (1H-benzimidazol-2-ylmethyl)-[5-(4-chloro-benzyl)-bicyclo[2.2.2]oct-2-yl]-amine as a racemic mixture of four diastereomers: MS (m+1)=380.9; $^1$H NMR (400 MHz, CDCl$_3$) 7.6 (br s, 1H), 7.2 (m, 4H), 7.05 (m, 2H), 4.04 and 4.06 (2×s, 2H), 2.85 (m, 1H), 2.6–5 (m, 3H), 2.0–1.0 (complex, 12H).

Example 7

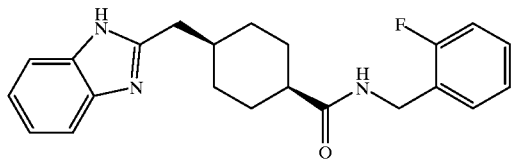

Cis-4-(1H-benzimidazol-2-ylmethyl)-cyclohexanecarboxylic acid 2-fluoroenzylamide Example 7 was prepared by the following procedure, referring to Scheme 4 above:

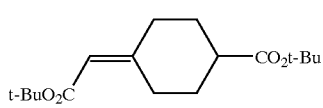
(B)

4-tert-Butoxycarbonylmethylene-cyclohexanecarboxylic acid ethyl ester (Compound B):

To a solution of ethyl 4-oxocyclohexanecarboxylate (Compound A) (8.3 g, 48.8 mmol), tert-butyl diethylphosphonoacetate (13.5 g, 53.7 mmol), and activated 4 Å sieves (30 g) in anhydrous THF (250 mL) at reflux was added anhydrous LiOH (3.8 g, 161.0 mmol) in small portions. After refluxing 6 h, the reaction was cooled and partitioned between water and ethyl acetate. The organic layer was dried with MgSO$_4$ and concentrated to give 13 g of a colorless oil. Flash chromatography on silica (10% EtOAc in hexane) yielded (B) 4-tert-butoxycarbonylmethylenecyclohexanecarboxylic acid tert-butyl ester (12.5 g, 95%) as a colorless oil. $^1$H NMR (400 MHz, CDCl$_3$) δ 5.60 (s, 1H), 4.15 (q, 2H), 3.60 (m, 1H), 2.55 (m, 1H), 2.35 (m, 1H), 2.21–2.02 (m, 4H), 1.78–1.62 (m, 2H), 1.48 (s, 9H), 1.25 (t, 3H); mass spectrum m/z 213 [(M-tBu)+; calcd for C$_{11}$H$_{17}$O$_4$: 213].

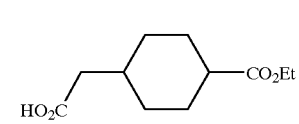
(C)

4-Carboxymethyl-cyclohexanecarboxylic acid ethyl ester (C):

A solution of diester (B) (12.5 g, 46.3 mmol) and 10% palladium on activated carbon (5 g) in absolute ethanol (200 mL) was exposed to a hydrogen atmosphere (at balloon pressure) and stirred vigorously for 1h. After removal of catalyst by filtration and concentration, the resultant colorless oil was dissolved in methylene chloride (150 mL) and TEA (75 mL) and stirred for 15 min. All volatiles were removed by rotary evaporation and the resultant colorless oil placed under high vacuum to give (C) 4-carboxymethyl-cyclohexanecarboxylic acid ethyl ester (9.9 g, 99%) as a white solid. Data for cis/trans mixture: $^1$H NMR (400 MHz, CD$_3$OD) δ 4.13 (2q, 4H), 2.58 (m, 1H), 2.30–2.20 (m, 1H), 2.20 (2d, 4H), 2.05–1.80 (m, 7H), 1.80–1.55 (m, 5H), 1.50–1.38 (m, 3H), 1.32–1.25 (m, 1H), 1.25 (2t, 6H), 1.10–1.00 (m, 2H); mass spectrum m/z 215 [(M+H)$^+$; calcd for C$_{11}$H$_{19}$O$_4$: 215].

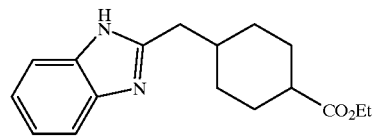
(D)

4-(1H-Benzoimidazol-2-ylmethyl)cyclohexanecarboxylic acid ethyl ester (D):

To a solution of acid (C) (10.5 g, 49.0 mmol), EDC (9.4 g, 49.0 mmol) and HOAt (6.7 g, 49.0 mmol) in 80 mL anhydrous DMF was added phenylenediamine (5.3 g, 49.0 mmol) and the reaction mixture stirred for 1h. The reaction mixture was partitioned between saturated aqueous NaHCO$_3$ and EtOAc and the organic portion washed 3× with water. The organic layer was dried with MgSO$_4$ and concentrated to yield 14 g of a yellow oil. The crude material was dissolved in toluene/TFA (1:1 300 mL), heated to 90° C. and stirred overnight. The reaction mixture was then concentrated and purified by column chromatography on silica using 1:1 EtOAc/hexane followed by 90:10:1 CH$_2$Cl$_2$/MeOH/NH$_4$OH to give (D) 4-(1H-benzimidazol-2-ylmethyl)-cyclohexanecarboxylic acid ethyl ester (7.5 g, 53%) as a colorless oil. Data for cis/trans mixture: $^1$H NMR (400 MHz, CDCl$_3$) δ 7.62 (2d, 4 H), 7.38 (2d, 4H), 2.70 (2d, 4H), 2.48 (m, 1H), 2.10–1.90 (m, 5H), 1.70–1.58 (m, 4 H), 1.60–1.53 (m, 3H), 1.49–1.38 (m, 4H), 1.63–1.50 (m, 1H), 1.40 (2t, 6H), 0.90–0.70 (m, 2H); mass spectrum m/z 287 [(M+H)$^+$; calcd for C$_{17}$H$_{23}$N$_2$O$_2$: 287].

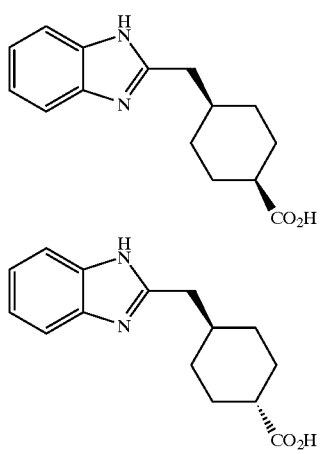

(E)

(F)

Cis-4-(1H-benzoimidazol-2-ylmethyl)-cyclohexanecarboxylic acid (E):

The cis/trans mixture of 4-(1H-benzimidazol-2-ylmethyl)-cyclohexanecarboxylic acid ethyl esters (D) (600 mg, 2.1 mmol) was dissolved in a minimal amount of THF (5 mL) and mixed with concentrated aqueous LiOH (2 mL). The reaction was stirred vigorously and heated at 65° C. for 3 h. After cooling and concentration, the crude material was dissolved in 1:1 water/CH$_3$CN and subjected to preparative reverse-phase HPLC to yield (E) cis-4-(1H-benzimidazol-2-ylmethyl)-cyclohexanecarboxylic acid (200 mg, 37%): $^1$H NMR (400 MHz, CD$_3$OD) δ 7.77 (m, 2 H), 7.60 (m, 2H), 3.11 (d, 2H), 2.62 (m, 1H), 2.10 (m, 3H), 1.65 (m, 4H), 1.43 (m, 2H); mass spectrum m/z 259 [(M+H)$^+$; calcd for C$_{15}$H$_{19}$N$_2$O$_2$: 259].

Later fractions gave the trans isomer (F) (276 mg, 51%): $^1$H NMR (400 MHz, CD$_3$OD) δ 7.77 (m, 2H), 7.59 (m, 2H), 3.08 (d, 2H), 2.28 (m, 1H), 2.05 (d, 2H), 1.95 (m, 1H), 1.84 (d, 2H), 1.46 (dq, 2H), 1.20 (dq, 2H); mass spectrum m/z 259 [(M+H)$^+$; calcd for C$_{15}$H$_{19}$N$_2$O$_2$: 259].

Example 7

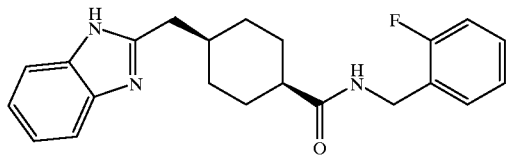

(Ex. 7)

Cis-4(1H-benzoimidazol-2-ylmethyl)-cyclohexanecarboxylic acid 2-fluoro-benzylamide:

To a solution of (E) cis-4-(1H-benzimidazol-2-ylmethyl)-cyclohexanecarboxylic acid (271 mg, 1.05 mmol), EDC (200 mg, 1.05 mmol) and HOAt (142 mg, 1.05 mmol) in anhydrous DMF (4 mL) was added 2-fluorobenzylamine (131 mg, 1.05 mmol) and the reaction mixture was stirred for 1h. The reaction mixture was partitioned between saturated aqueous NaHCO$_3$ and EtOAc and the organic layer washed 2× with water. The EtOAc was dried with MgSO$_4$ and concentrated to give a yellow solid. The crude material was triturated with 2:2:1 water/CH$_3$CN/DMSO and the resultant white solid filtered off. Repetitive concentration and trituration of the filtrate in the same manner gave cis-4-(1H-benzimidazol-2-ylmethyl)-cyclohexanecarboxylic acid 2-fluoro-benzylamide (F) (230 mg, 60%) as a white solid. The (F) compound was stirred in 1M HCl/ether (10 ML) for 1 h and concentrated to give the HCl salt of Ex. 7 (250 mg): $^1$H NMR (400 MHz, CD$_3$OD) δ 7.50 (br s 2H), 7.35–7.25 (m, 2H), 7.22–7.05 (m, 4H), 4.43 (s, 2H), 2.92 (d, 2H), 2.41 (m, 1H), 2.23 (m, 1H), 1.93 (m, 2H), 1.60 (m, 6H); mass spectrum m/z 366 [(M+H)$^+$; calcd for C$_{22}$H$_{25}$N$_3$OF: 366].

Example 8

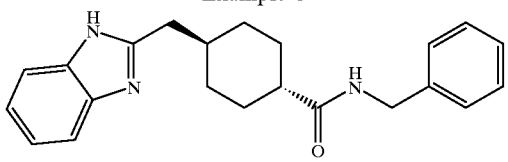

Trans-4-(1H-benzoimidazol-2-ylmethyl)-cyclohexanecarboxylic acid 2-fluoro-benzylamide Example 8 was prepared by the following procedure. To a solution of trans-4-(1H-benzimidazol-2-ylmethyl)-cyclohexanecarboxylic acid (F) (444 mg, 1.72 mmol), EDC (328 mg, 1.72 mmol) and HOAt (234 mg, 1.72 mmol) in anhydrous DMF (4 mL) was added benzylamine (184 mg, 1.72 mmol). The resulting reaction mixture was stirred for 15 h. The reaction mixture was partitioned between saturated aqueous NaHCO$_3$ and EtOAc and the organic layer washed 2× with water, and dried with MgSO$_4$. Concentration gave trans-4-(1H-benzimidazol-2-ylmethyl)-cyclohexanecarboxylic acid benzylamide (400 mg, 67%) as a white solid. $^1$H NMR (400 MHz, CD$_3$OD) δ 7.49 (br s, 2H), 7.30–7.17 (m, 7H), 4.34 (s, 2H), 2.78 (d, 2H), 2.21 (m, 1H), 1.84 (m, 5H), 1.55 (q, 2H), 1.16 (q, 2H); mass spectrum m/z 348 [(M+H)$^+$; calcd for C$_{22}$H$_{26}$N$_3$O: 348].

All compounds analogous to Example 8 were prepared from carboxylic acid (F) via the above procedure using the appropriate amine and purified by reverse-phase HPLC.

Compounds of the present invention can be prepared according to Scheme 7 shown below:

Scheme 7

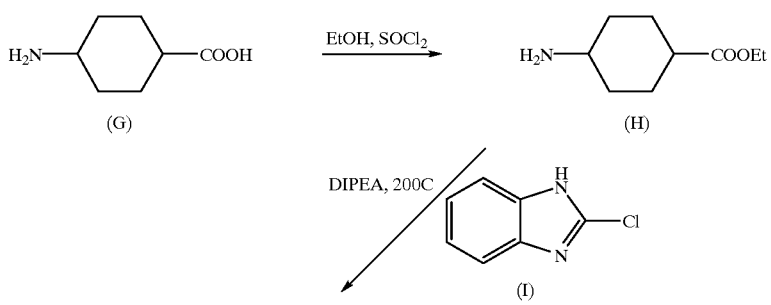

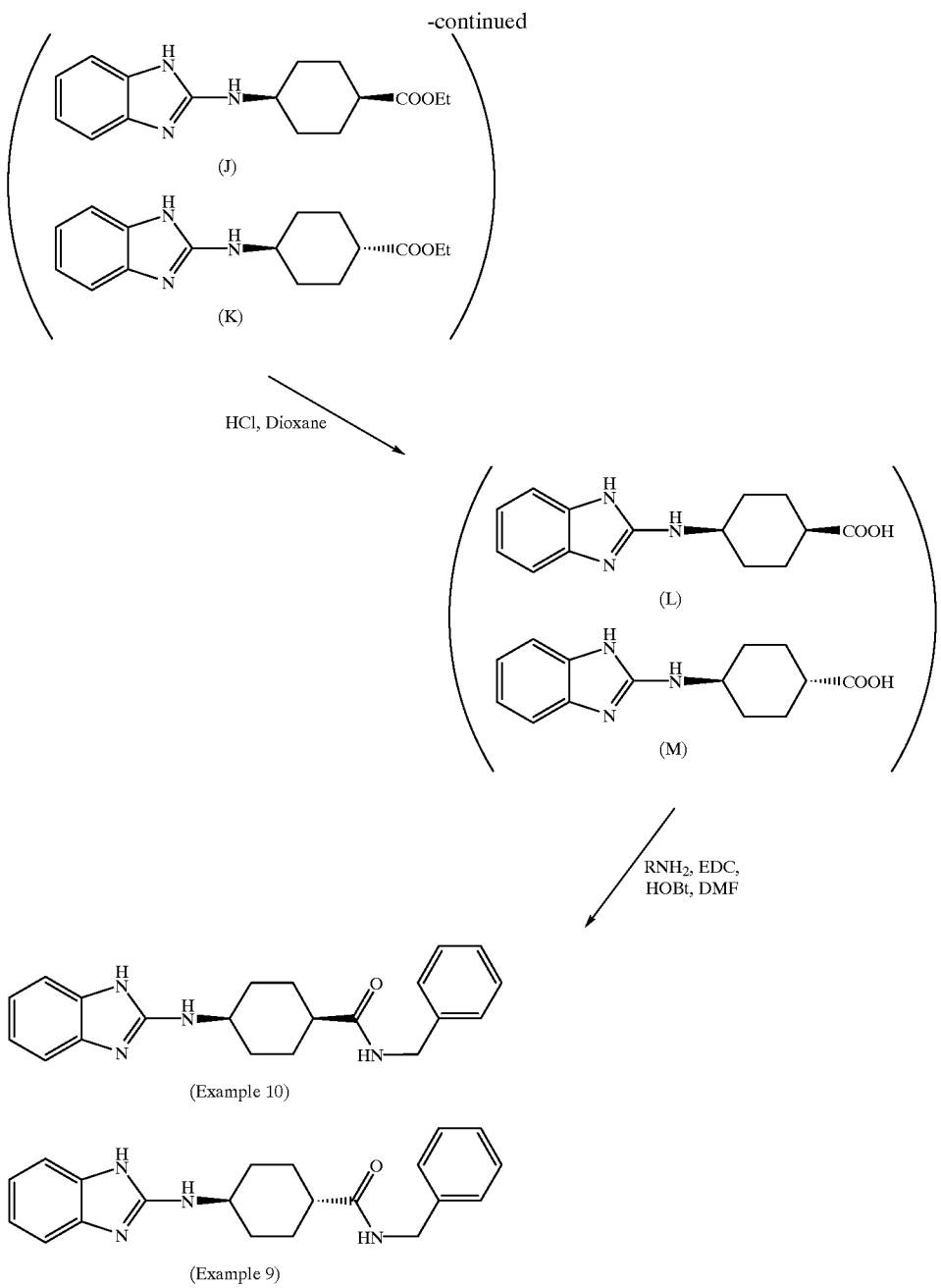

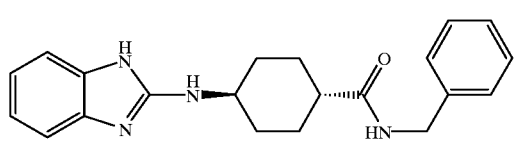

Trans-4-(1H-benzimidazol-2-ylamino)-cyclohexanecarboxylic acid benzylamide

Referring to Scheme 7 above, Example 9 was prepared by the following procedure.

4-Amino-cyclohexanecarboxylic acid ethyl ester (H):

To a suspension of 4-amino-cyclohexanecarboxylic acid (G) (5 g, 35 mmol) in EtOH (175 mL) at 0° C. was added $SOCl_2$ (12.6 mL, 174 mmol) dropwise via a syringe. The reaction mixture was warmed to room temperature and stirred for 16 h. After concentration of the reaction mixture, ether was added and the suspension was filtered to give 4-amino-cyclohexanecarboxylic acid ethyl ester (H) (mixture of cis/trans) as a white solid (4.8 g): $^1H$ NMR (300Mz, $CDCl_3$) δ 8.35 (br s, 3H), 4.18 (m, 2H), 3.36–3.15

(m, 1H), 2.54 (m, 1H), 2.30–1.45 (series of m, 1H), 1.13 (t, 3 H); mass spectrum m/z 172 [(M+H)$^+$; calcd for C$_9$H$_{18}$NO$_2$: 172].

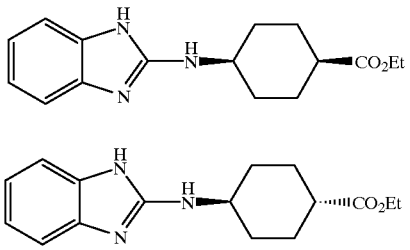

Cis-4-(1H-benzimidazol-2-ylamino)-cyclohexanecarboxylic acid ethyl ester (J) and Trans-4-(1H-benzimidazol-2-ylamino)-cyclohexanecarboxylic acid ethyl ester (K):

A mixture of 2-Chlorobenzimidazole (I) (0.9 g, 5.9 mmol) and ethyl-4-amino-cyclohexane carboxylate (1.1 g, 5.4 mmol) were placed in a glass high pressure a tube. Diisopropylethylamine (2.8 mL, 16.2 mmol) was added, the reaction vessel was sealed and heated to 200° C. for 4 h and allowed to cool to room temperature. Next was added 5 mL EtOH and heated to dissolve the reaction mixture. The reaction mixture was partitioned between aqueous NaHCO$_3$ and EtOAc, and the organic layer was washed with water and brine, dried over MgSO$_4$, filtered and concentrated. Purification of the crude product on silica gel (gradient, 1:1 hexanes:EtOAc to EtOAc) gave the cis 4-(1H-benzimidazol-2-ylamino)-cyclohexanecarboxylic acid ethyl ester (J) (0.5 g) and the trans 4-(1H-benzimidazol-2-ylamino)-cyclohexanecarboxylic acid ethyl ester (K) (0.5 g) Data for (J): $^1$H NMR (300 MHz, CDCl$_3$) δ 7.28 (br s, 2H), 7.02 (m, 2H), 5.16 (br s, 1H), 4.15 (q, 2H), 3.97 (br s, 1H), 2.40 (br s, 1H), 1.80–1.54 (m, 8H), 1.22 (t, 3H); mass spectrum m/z 288 [(M+H)$^+$; calcd for C$_{16}$H$_{22}$N$_3$O$_2$: 288]. Later fractions gave the trans isomer (K) (0.5 g): $^1$H NMR (300MH, CDCl$_3$) δ 7.28 (br s, 2H), 7.02 (m, 2H), 4.82 (br s, 1H), 4.15 (q, 2H), 3.64 (m, 1H), 2.20 (br d, 3H), 1.96 (br d, 2H), 1.42 (m, 2H), 1.22 (t, 3 H), 1.20 (m, 2H); mass spectrum m/z 288 [(M+H)$^+$; calcd for C$_{16}$H$_{22}$N$_3$O$_2$: 288].

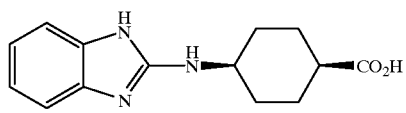

Trans-4-(1H-benzimidazol-2-ylamino)-cyclohexanecarboxylic acid (M):

A solution of trans 4-(1H-benzimidazol-2-ylamino)-cyclohexanecarboxylic acid ethyl ester (K) (500 mg, 1.7 mmol) in dioxane (4 mL) and HCl (6 N, 8 mL) was heated to 60° C. for 16 h. After cooling, concentration of the reaction mixture gave trans 4-(1H-benzimidazol-2-ylamino)-cyclohexanecarboxylic acid as a white solid (M) (420 mg): $^1$H NMR (300 MHz, CD$_3$OD) δ 7.39 (m, 2H), 7.28 (m, 2H), 3.57 (m, 1H), 2.35 (m, 1H), 2.18 (br t, 4H), 1.65–1.40 (m, 4H); mass spectrum m/z 260 [(M+H)$^+$; calcd for C$_{14}$H$_{18}$N$_3$O$_2$: 260].

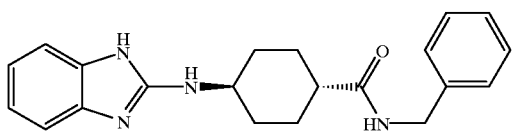

Example 9, Trans-4-(1H-benzimidazol-2-ylamino)-cyclohexanecarboxylic acid benzylamide:

To a solution of trans 4-(1H-benzimidazol-2-ylamino)-cyclohexanecarboxylic acid (M) (20 mg, 0.07 mmol) in DMF (0.2 mL) was added EDC (26 mg, 0.14 mmol), HOBt (18 mg, 0.14 mmol), triethylamine (0.007 mL, 0.14 mmol) and benzyl amine (0.007 mL, 0.7 mmol). The reaction mixture was stirred at room temperature for 1 h followed by quenching with aqueous NaHCO$_3$ and EtOAc. The layers were separated and the organic was washed twice with water, dried over Na$_2$SO$_4$, filtered and concentrated. Purification of the crude oil by preparative reverse-phase HPLC gave trans 4-(1H-benzimidazol-2-ylamino)-cyclohexanecarboxylic acid benzylamide (Example 9) (14 mg): $^1$H NMR (300 MHz, CD$_3$OD) δ 7.40–7.20 (m, 9H), 4.39 (s, 2H), 3.55 (m, 1H), 2.31 (m, 1H), 2.20 (br d, 2H), 1.98 (br d, 2H), 1.77 (m, 2H), 1.50 (m, 2H); mass spectrum m/z 349 [(M+H)$^+$; calcd for C$_{21}$H$_{25}$N$_4$O: 349].

Example 10

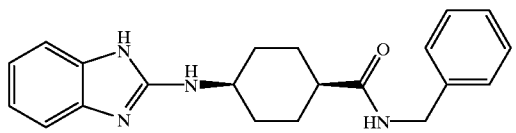

Example 10, Cis4-(1H-benzoimidazol-2-ylamino)-cyclohexanecarboxylic acid benzylamide:

Referring to Scheme 7, Example 10 was prepared by the following procedure.

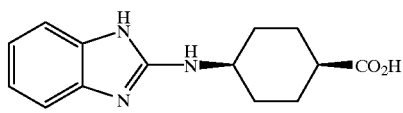

Cis-4-(1H-benzimidazol-2-ylamino)-cyclohexanecarboxylic acid (L):

In a similar manner to Example 9 above, cis 4-(1H-benzimidazol-2-ylamino)-cyclohexanecarboxylic acid ethyl ester (J) was saponified and gave the cis 4-(1H-benzimidazol-2-ylamino)-cyclohexanecarboxylic acid (L): $^1$H NMR (300MHz, CD$_3$OD) δ 7.39 (m, 2H), 7.28 (m, 2H), 3.64 (m, 1H), 2.60 (m, 1H), 2.10 m, 2 1), 1.95 (m, 2H), 1.81–1.65 (m, 4H); mass spectrum m/z 260 [(M+H)$^+$; calcd for C$_{14}$H$_{18}$N$_3$O$_2$: 260].

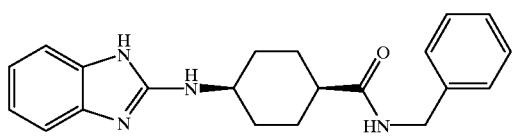

Example 10, Cis-4-(1H-benzoimidazol-2-ylamino)-cyclohexanecarboxylic acid benzylamide:

To a solution of cis 4-(1H-benzimidazol-2-ylamino)-cyclohexanecarboxylic acid (L) (20 mg, 0.07 mmol) in DMF (0.2 mL) was added EDC (26 mg, 0.14 mmol), HOBt (18 mg, 0.14 mmol), triethylamine (0.019 mL, 0.14 mmol) and benzyl amine (0.007 mL, 0.7mmol). The reaction mixture was stirred at room temperature for 1h followed by quenching with aqueous NaHCO$_3$ and EtOAc. The layers were separated and the organic was washed twice with water, dried over Na$_2$SO$_4$, filtered and concentrated. Purification of the crude oil by preparative reverse-phase HPLC gave cis 4-(1H-benzimidazol-2-ylamino)-cyclohexanecarboxylic acid benzylamide (Example 10) (12 mg): $^1$H NMR (300 MHz, CD$_3$OD) δ 7.40–7.20 (m, 9H), 4.39 (s, 2H), 3.81 (m, 1H), 2.45 (m, 1H), 2.02–1.77 (m, 8H); mass spectrum m/z 349 [(M+H)$^+$; calcd for C$_{21}$H$_{25}$N$_4$O: 349].

All compounds analogous to Example 10 were prepared from carboxylic acid (M) via the above procedure using the appropriate amine and purified by reverse-phase HPLC.

Example 11

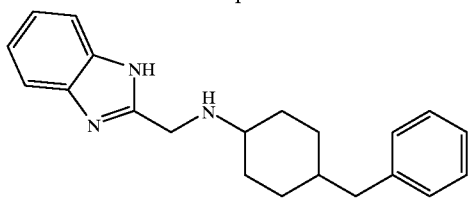

(1H-Benzimidazol-2-ylmethyl)-(4-benzyl-cyclohexyl)-amine

Example 11 was prepared in a manner similar to Example 5, but substituting 4-benzyl-cyclohexanone, the product of Example 1, Step 3, for exo and * endo 3-(4-chloro-benzyl)-bicyclo[3.2.1]octan-8-one. The procedure gave a 1:1 mixture of cis and trans (1H-benzoimidazol-2-ylmethyl)-(4-benzyl-cyclohexyl)-amine. Chromatography on Chiralpaka™ OD eluting with 60:40 of 0.1% diethylamine in hexane:2-propanol gave first (1H-benzoimidazol-2-ylmethyl)-(4-cis-benzyl-cyclohexyl)-amine: RT=4.69 min; MS (m+1)=320; $^1$H NMR (400 MHz, CDCl$_3$) δ 7.6 (m, 2H), 7.35–7.25 (in, 5H), 7.18 (m, 2H), 4.2 (s, 2H), 2.85 (m, 1H), 2.55 (d, 21), 1.75 (m, 3H), 1.7–1.55 (m, 2H), 1.5 (m, 2H), 1.4 (m, 3H).

Later fractions gave (1H-benzoimidazol-2-ylmethyl)-(4-trans-benzyl-cyclohexyl)-amine: RT=5.67 min; MS (m+1)= 320; $^1$H NMR (400 MHz, CDCl$_3$) δ 7.6 (m, 2H), 7.35–7.25 (m, 5H), 7.18 (m, 2H), 4.2 (s, 2H), 2.5 (d, 2H), 1.95 (d, 2H), 1.72 (d, 2H), 1.7–1.55 (m, 2H), 1.5 (m, 2H), 1.4 (m, 3H).

Example 12

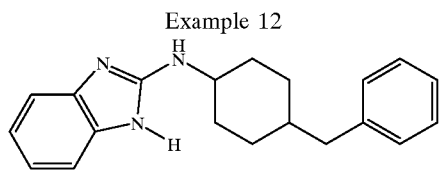

(1H-Benzimidazol-2-yl)-(4-benzy]-cyclohexyl)-amine

Example 12 was prepared by the following procedure.
Step 1:

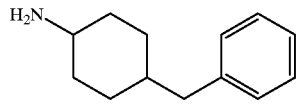

4-Benzyl-cyclohexylamine:

A mixture of 2 g of 4-benzylcyclohexanone, the product of Example 1, Step 3, 16 g of ammonium acetate, 100 mL of methanol and 2.5 g of sodium cyanoborohydride was stirred for 5 days at room temperature. After cooling in an ice bath, the reaction was carefully quenched in an efficient fume hood by dropwise addition of 25 mL of 1N HCl. After stirring for 10 min, sodium hydroxide pellets were added to the cold solution until the pH (indicator paper) was about 10. The mixture was concentrated under reduced pressure, diluted with 100 mL of water, made basic by addition of more sodium hydroxide pellets and extracted into 4×100 mL portions of chloroform. After drying over magnesium sulfate, the extracts were concentrated X under reduced pressure and then dried under vacuum overnight. Analysis by TLC (silica gel, elution with 90:10:1 chloroform:methanol:conc. ammonium hydroxide) indicated no 4-benzylcyclohexanone or 4-benzylcyclohexanol was present, only 2 new bands which correspond to a mixture of cis- and trans 4-benzyl-cyclohexylamine, which was an oil.
Step 2:

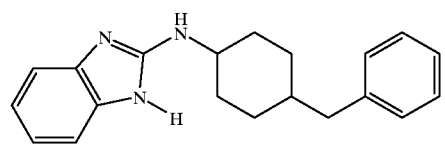

(1H-Benzimidazol-2-yl)-(4-benzyl-cyclohexyl)-amine:

Following the sample experimental procedure described by J. J. Perkins, A. E. Zartman, and R. S. Meissner, *Tetrahedron Letters*, 40:1103–1106(1999), but substituting a mixture of cis- and trans 4-benzyl-cyclohexylaamine for cyclohexylamine, gave a mixture of cis and trans (1H-benziimidazol-2-yl)-(4-benzyl-cyclohexyl)-amine. Chromatography on silica gel eluting with 90:10 cbloroform:methanol gave (1H-benziimidazol-2-yl)-(4-cis-benzyl-cyclohexyl)-amine: MS (m+1)=306; $^1$H NMR (400 MHz, CDCl$_3$) δ 2.42 (d, 2H), 2.10 (d, 2H), 1.70 (d, 2H).

Later fractions gave (1H-benziimidazol-2-yl)-(4-trans-benzyl-cyclohexyl)-amine: MS (m+1)=306; $^1$H NMR (400 MHz, CDCl$_3$) δ 2.55 (m, 2H), 2.15 (d, 2H), 1.70 (d, 2H).

Example 13

Ex. 13

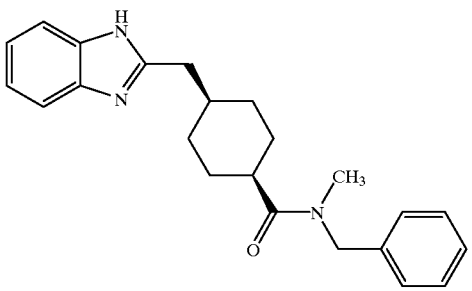

Example 13 was prepared by following the above procedure for Example 7 except using N-methylbenzylamine instead of 2-fluorobenzylamine: mass spectrum m/z 361 [(M+H)$^+$; calcd for C$_{23}$H$_{28}$N$_3$O: 362].

Compounds of the present invention can be prepared according to Scheme 8 shown below:

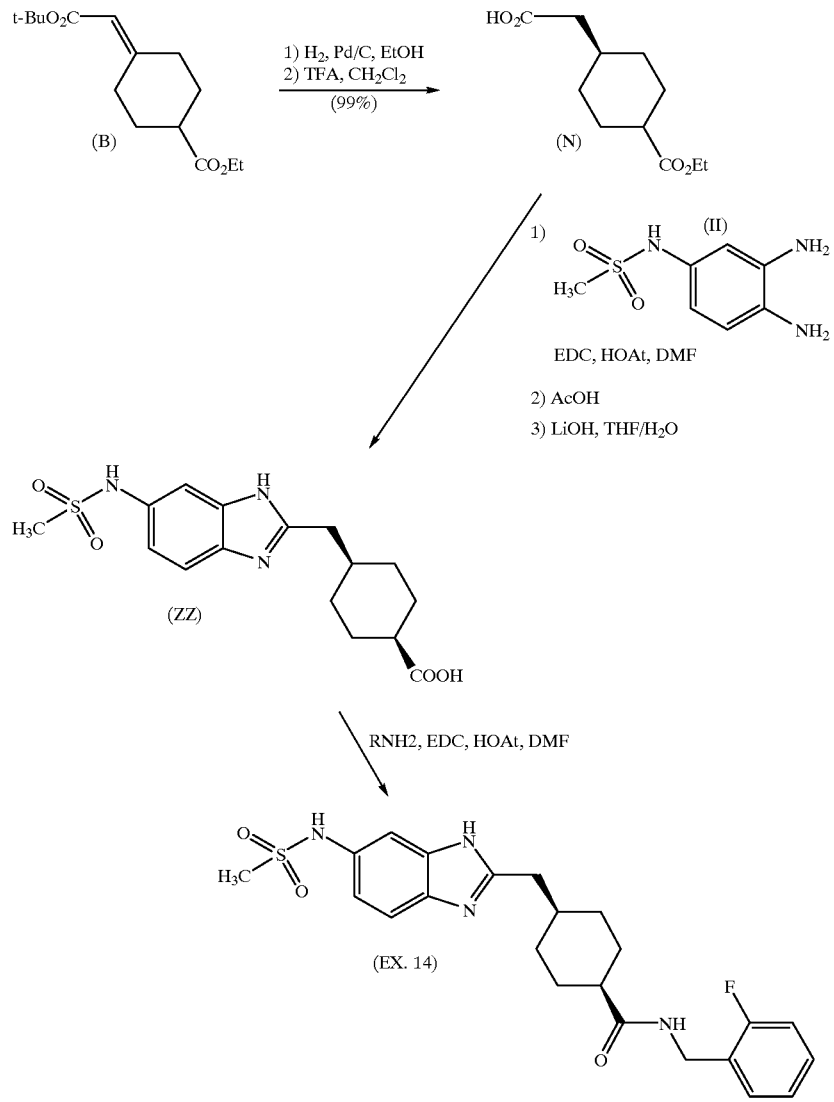

Compound (N)

Olefin (B) (0.3 g, 1.18 mmol) was dissolved in EtOAc (5 mL) and cooled to −20° C. Rh on alumina catalyst (0.06 g) was added, the reaction vessel was pressurized to 1500 psi with hydrogen gas, and the mixture was shaken for 5 h. After removal of the catalyst by filtration and concentration, the resultant colorless oil was dissolved in methylene chloride (5 mL) and TFA (3 mL) and stirred for 15 min. All volatiles were removed by rotary evaporation and the resultant colorless oil placed under high vacuum to give Compound (N) as a 6:1 cis to trans mixture.

Compound (ZZ)

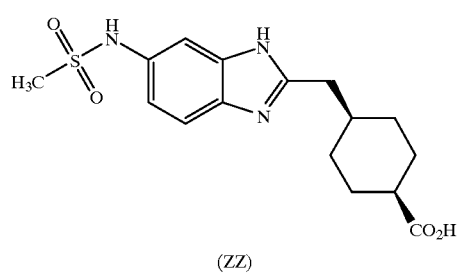

To a solution of acid (N) (300 mg, 1.4 mmol) in DM (10 mL) was added EDC (268 mg, 1.40 mmol), HOAt (190 mg, 1.40 mmol) and methanesulfonic acid (3,4-diaminophenyl)-amide (II) (281 mg, 1.40 mmol). The reaction mixture was stirred at room temperature for 16 h followed by quenching with aqueous NaHCO$_3$ and EtOAc. The layers were separated and the organic was washed twice with water, dried over Na$_2$SO$_4$, filtered and concentrated.

The resulting crude product was dissolved in acetic acid (10 mL) and a heated to 130° C. for 15 min. The reaction mixture was cooled, concentrated and partitioned between aqueous NaHCO$_3$ and EtOAc. The organic layer was dried over Na$_2$SO$_4$, filtered and concentrated. The crude oil was used without purification.

The crude ester was dissolved in HBr/H$_2$0 (48%, 10 mL) and was then heated to 100° C. for 30 min. The resulting reaction mixture was cooled, concentrated and purified by preparative reverse-phase HPLC, to give Compound (ZZ) as the pure cis isomer: $^1$H NMR (300 MHz, CD$_3$OD) δ 7.75 (d, 1H), 7.69 (d, 1H), 7.39 (dd, 1H), 3.09 (d, 2H), 2.99 (s, 3H), 2.60 (m, 1H), 2.08 (m, 3H), 1.62 (m, 4H);1.40 (m, 2H) ppm; mass spectrum m/z 352 [(M+H)$^+$; calcd for C$_{16}$H$_{22}$N$_3$O$_4$S: 352].

Example 14

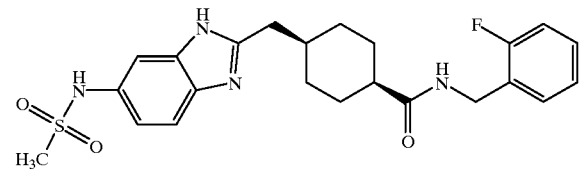

EXAMPLE 14

Example 14 was prepared by the following procedure: To a solution of (ZZ) (10 mg, 0.03 mmol), EDC (10 mg, 0.06 mmol) and HOAt (8 mg, 0.06 mmol) in anhydrous DMF (0.3 mL) was added 2-fluorobenzylamine (2 mg, 0.06 mmol) and the reaction mixture was stirred for 2 h. The reaction mixture was partitioned between saturated aqueous NaHCO$_3$ and EtOAc. The organic layer was washed 2× with water. The EtOAc was dried with MgSO$_4$ and concentrated. The resulting crude material was purified by reverse phase HPLC to give Example 14: mass spectrum n/z 459 [(M+H)$^+$; calcd for C$_{23}$H$_{28}$FN$_4$O$_3$S: 459].

Example 15

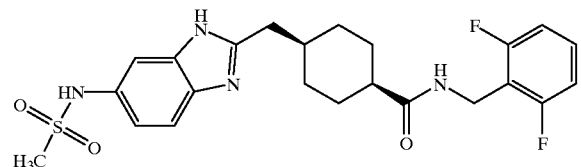

EXAMPLE 15

Example 15 was prepared by following the above procedure for Example 14 except 2,6-diflouorobenzylamine was used instead of 2-fluorobenzylamine: mass spectrum m/z 477 [(M+H)$^+$; calcd for C$_{23}$H$_{27}$F$_2$N$_4$O$_3$S: 477].

COMPOUND (ZZ1)

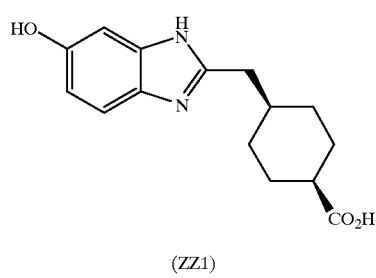

(ZZ1)

Compound (ZZ1) was prepared by following the above procedure for Compound (ZZ) except 4-methoxy-1,2-phenylenediamine was used instead of methanesulfonic acid (3,4-diamino-phenyl)-amide: mass spectrum m/z 275 [(M+H)$^+$; calcd for $C_{15}H_{19}N_2O_3$: 275].

Example 16

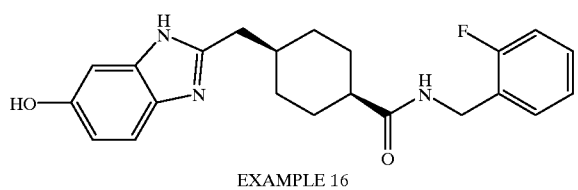

EXAMPLE 16

Example 16 was prepared by following the above procedure for Example 14 except Compound (ZZ1) was used instead of Compound (ZZ): mass spectrum m/z 382 [(M+H)$^+$; calcd for $C_{22}H_{24}FN_3O_2$: 382].

Example 17

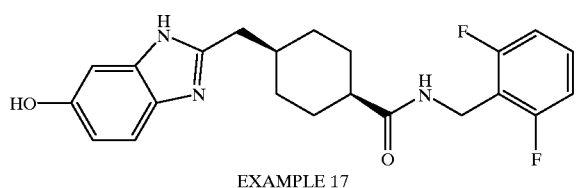

EXAMPLE 17

Example 17 was prepared by following the above procedure for Example 15 except Compound (ZZ1) was used instead of Compound (ZZ): mass spectrum m/z 400 [(M+H)$^+$; calcd for $C_{22}H_{24}F_2N_3O_2$: 400].

Compound (ZZ2)

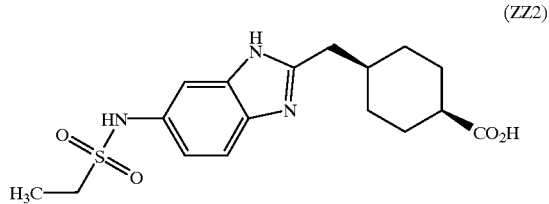

(ZZ2)

Compound (ZZ2 was prepared by following the above procedure for Compound (ZZ) except ethanesulfonic acid (3,4-diamino-phenyl)-amide was used instead of methanesulfonic acid (3,4-diamino-phenyl)-amide: mass spectrum m/z 366 [(M+H)$^+$; calcd for $C_{17}H_{24}N_3O_4S$: 366].

Example 18

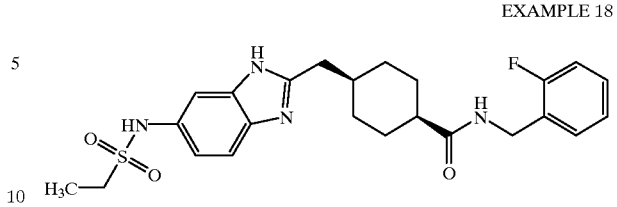

EXAMPLE 18

Example 18 was prepared by following the above procedure for Example 14 except Compound (ZZ2) was used instead of Compound (ZZ): mass spectrum m/z 473 [(M+H)$^+$; calcd for $C_{24}H_{30}FN_4O_3S$: 473].

Example 19

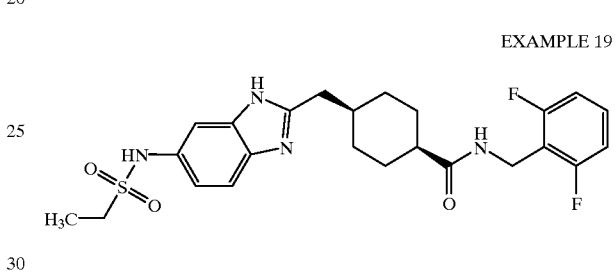

EXAMPLE 19

Example 19 was prepared by following the above procedure for Example 15 except Compound (ZZ2) was used instead of Compound (ZZ): mass spectrum m/z 491 [(M+H)$^+$; calcd for $C_{24}H_{29}F_2N_4O_3S$: 491].

Compounds of the present invention can be prepared according to Scheme 9 shown below:

Example 20

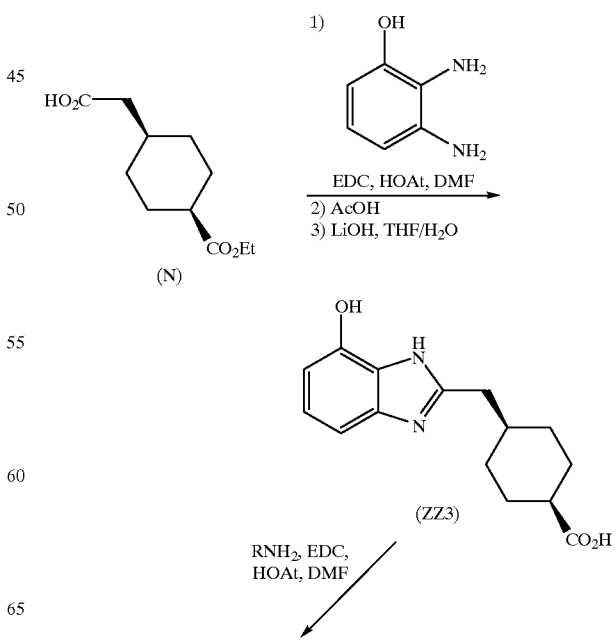

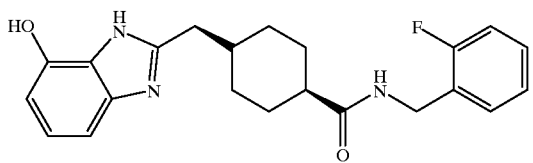

EXAMPLE 20

Preparation of acid Compound (ZZ3):

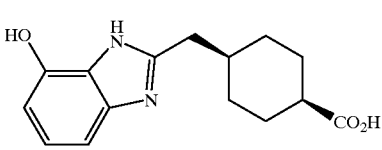

(ZZ3)

Compound (ZZ3) was prepared by following the above procedure for Compound ZZ except 3-hydroxy-1,2-phenylenediamine was used instead of methanesulfonic acid (3,4-diamino-phenyl)-amide: mass spectrum m/z 275 [(M+H)$^+$; calcd for $C_{15}H_{19}N_2O_3$: 275].

Example 20

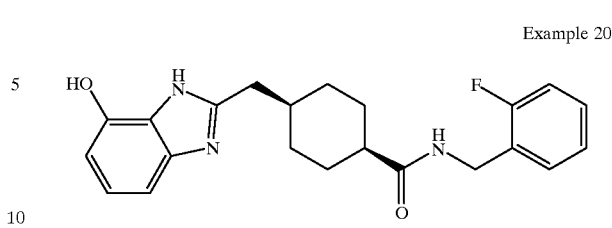

Example 20

Example 20 was prepared by following the above procedure for Example 14 except Compound (ZZ3) was used instead of Compound (ZZ): mass spectrum m/z 382 [(M+H)$^+$; calcd for $C_{22}H_{25}FN_3O_2$: xx].

Example 21

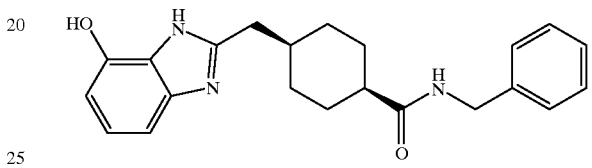

Example 21

Example 20 was prepared by following the above procedure for Example 14 except Compound (ZZ3) was used instead of Compound (ZZ), and benzylamine was used instead of 2-fluorobenzylamine: mass spectrum m/z 364 [(M+H)$^+$; calcd for $C_{22}H_{26}N_3O_2$: 364].

Compounds of the present invention can be prepared according to Scheme 10 shown below:

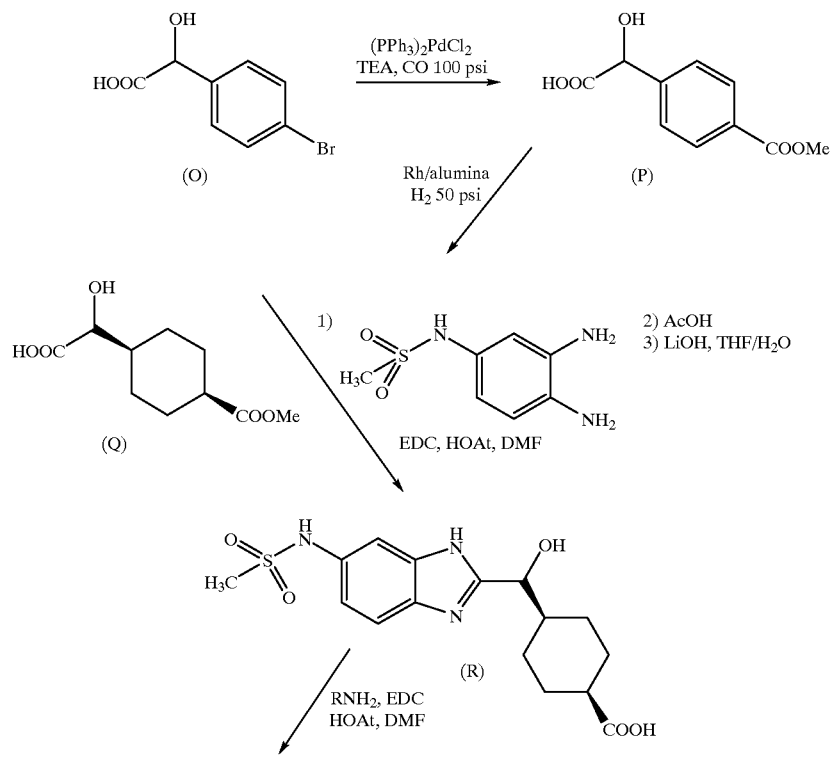

-continued

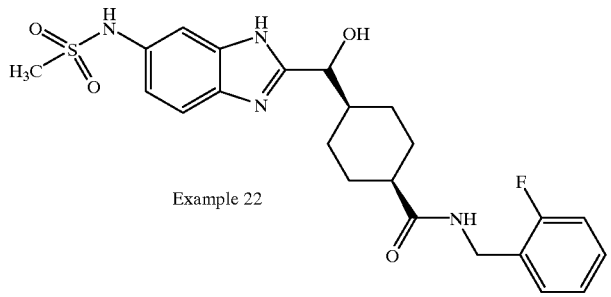

Example 22

Compound (Q):

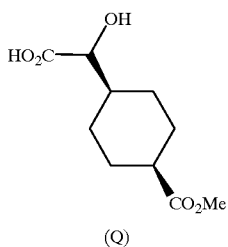

(Q)

4-Bromomandelic acid (O) (3.0 g, 13.0 mmol) was dissolved in MeOH (75 mL) and placed in a pressure bomb. To that resulting solution was added $(PPh_3)_2PdCl_2$ (0.91 g, 1.3 mmol) and triethylamine (5.4 mL, 39 mmol). The reaction mixture was pressurized with CO (100psi) and heated to 100° C. for 60 h. After cooling, the mixture was filtered, concentrated and purified by reverse phase HPLC to give ester (P): $^1$H NMR (400 MHz, $CD_3OD$) δ 8.03 (d, 2H), 7.61 (d, 2H), 5.25 (s, 1 H), 3.90 (s, 3H) ppm.

Compound (P) (0.35 g, 1.7 mmol) was dissolved in MeOH (10 mL) and Rh on alumina catalyst (0.05 g) was added. The reaction vessel was pressurized to 50 psi with hydrogen gas, and the mixture was shaken for 24 h. After filtration and concentration, the product (Q) was used without purification as a 3:1 cis:trans mixture of isomers: mass spectrum m/z 217 [(M+H)$^+$; calcd for $C_{10}H_{17}O_5$: 217].

Compound (R):

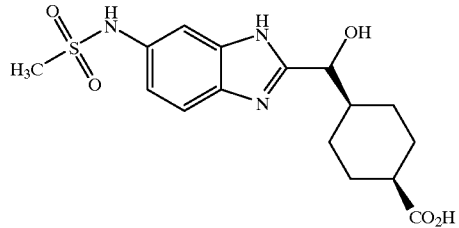

(R)

To a solution of acid (Q) (100 mg, 0.46 mmol) in DMF (6 mL) was added EDC (97 mg, 0.51 mmol), HOAt (70 mg, 0.51 mmol) and methanesulfonic acid (3,4-diaminophenyl)-amide (II) (100 mg, 0.46 mmol). The reaction mixture was stirred at room temperature for 1h followed by quenching with aqueous $NaHCO_3$ and EtOAc. The layers were separated and the organic was washed twice with water, dried over $Na_2SO_4$, filtered and concentrated.

The resulting crude product was dissolved in acetic acid (5 mL) and heated to 130° C. for 15 min. The reaction mixture was cooled, concentrated and partitioned between aqueous $NaHCO_3$ and EtOAc. The organic layer was dried over $Na_2SO_4$, filtered and concentrated. The resulting crude oil was without purification The crude ester was dissolved in $HBr/H_2O$ (48%, 3 mL) and then was heated to 100° C. for 10 min. The reaction mixture was cooled, concentrated and purified by preparative reverse-phase HPLC, to give (R) as the pure cis isomer: mass spectrum m/z 368 [(M+H)$^+$; calcd for $C_{16}H_{22}N_3O_5S$: 368].

Example 22

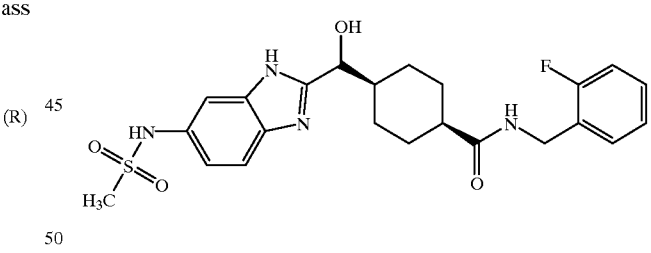

Example 22

Example 22 was prepared by the following procedure: To a solution of (R) (35 mg, 0.1 mmol), EDC (36 mg, 0.2 mmol) and HOAt (26 mg, 0.2 mmol) in anhydrous DMF (2 mL) was added 2-fluorobenzylamine (24 mg, 0.2 mmol) and the resulting reaction mixture was stirred for 3 h. The reaction mixture was then partitioned between saturated aqueous $NaHCO_3$ and EtOAc, and the organic layer washed 2× with water. The EtOAc was dried with $MgSO_4$ and concentrated. The resulting crude material was purified by reverse phase HPLC to give Example 22: $^1$H NMR (300 MHz, $CD_3OD$) δ 7.74 (m, 2H), 7.41 (d, 1H), 7.25 (m, 2H); 7.09 (m, 2H), 5.06 (d, 1H), 4.40 (s, 2H), 3.00 (s, 3H), 2.47 (m, 1H), 2.10 (m, 3H), 1.6 (m, 6H) ppm; mass spectrum m/z 475 [(M+H)$^+$; calcd for $C_{23}H_{28}FN_4O_4S$: 475].

Example 23

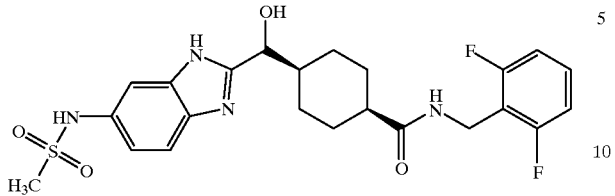

Example 23 was prepared by following the above procedure for Example 22 except 2,6-diflouorobenzylamine was used instead of 2-fluorobenzylamine: mass spectrum m/z 493 [(M+H)$^+$; calcd for $C_{23}H_{27}F_2N_4O_4S$: 493].

Compound (S):

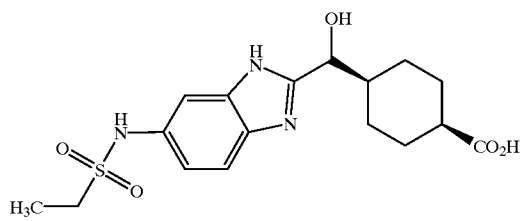

Compound (S) was prepared by following the above procedure for (R) except ethanesulfonic acid (3,4-diamino-phenyl)-amide was used instead of methanesulfonic acid (3,4-diamino-phenyl)-amide: mass spectrum m/z 382 [(M+H)$^+$; calcd for $C_{17}H_{24}N_3O_5S$: 382].

Example 24

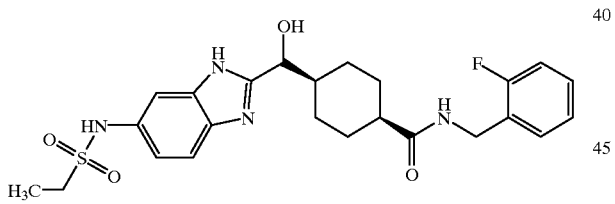

Example 24 was prepared by following the above procedure for Example 22 except acid (S) was used instead of (R): mass spectrum m/z 489 [(M+H)$^+$; calcd for $C_{24}H_{30}FN_4O_4S$: 489].

Example 25

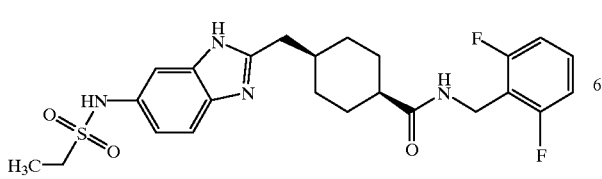

Example 25 was prepared by following the above procedure for Example 23 except acid Compound (S) was used instead of Compound (R): mass spectrum m/z 507 [(M+H)$^+$; calcd for $C_{24}H_{29}F_2N_4O_4S$: 507].

Compound (T):

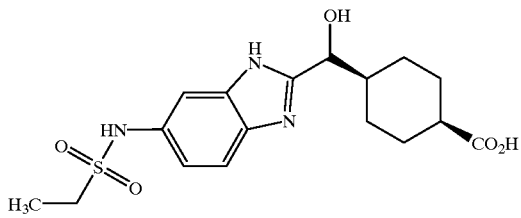

Acid (T) was prepared by following the above procedure for Compound (R) except phenylene diamine was used instead of methanesulfonic acid (3,4-diamino-phenyl)-amide: mass spectrum m/z 275 [(M+H)$^+$; calcd for $C_{15}H_{19}N_2O_3$: 275].

Example 26

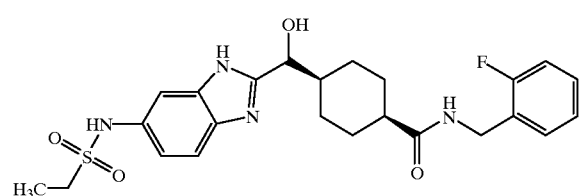

Example 26 was prepared by following the above procedure for Example 22 except acid (T) was used instead of Compound (R): mass spectrum m/z 382 [(M+H)$^+$; calcd for $C_{22}H_{25}FN_3O_2$: 382].

Examples 26a and 26b:

Racemate Example 26 was separated into its enantiomers by chiral HPLC on a Chiralpack AD column (250×4.6 cm) eluting with 75% hexane +0.1% diethylamine and 25% 2-propanol. The faster eluting compound was Example 26a. The slower eluting compound was Example 26b.

Example 27

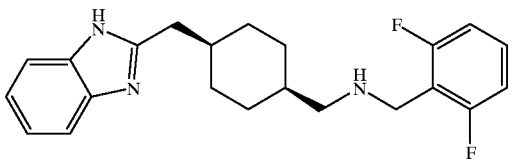

Example 27 was prepared by the following procedure: To a solution of amide (This does not seem to be an Example above) L-478,227 (200 mg, 0.52 mmol) in THF (1 mL) was added BH3-THF (1M, 5.0 mL). The reaction mixture was heated to 50° C. for 12 h, cooled and carefully quenched with HCl (1M). The resulting mixture was partitioned between EtOAc/aqueous $NaHCO_3$. The organic layer was dried over $Na_2SO_4$, filtered, concentrated and purifed by reverse phase HPLC to give Example 27: $^1$H NMR (400 MHz, $CD_3OD$) δ 7.71 (m, 2H), 7.57 (m, 3 H), 7.18 (t, 2H); 4.35 (s, 2H), 3.14 (t, 4H), 2.21 (m, 1H), 2.00 (m, 1H), 1.75–1.40 (m, 8H) ppm; mass spectrum n/z 370 [(M+H)$^+$; calcd for $C_{22}H_{26}F_2N_3$: 370].

Example 28

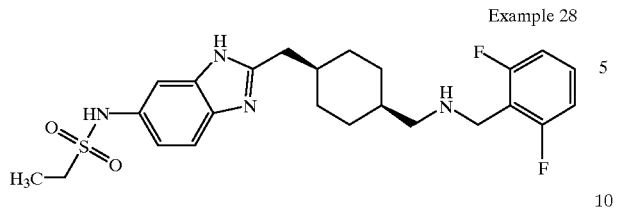

Example 28

Example 28 was prepared by following the above procedure for Example 27 except acid Example 19 was used instead of L-478,227: mass spectrum m/z 477 [(M+H)$^+$; calcd for $C_{24}H_{31}F_2N_4O_2S$: 477].

Compounds of the present invention can be prepared according to Scheme 11 shown below:

Compound (V):

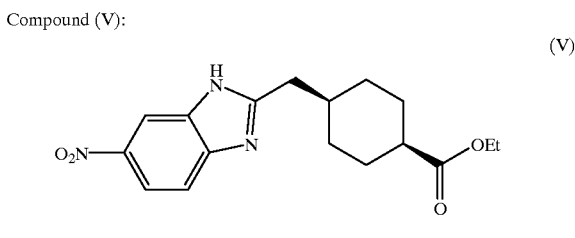

Compound (V) was prepared by the following procedure: To a solution of acid (N) (900 mg, 4.2 mmol) in DMF (10 mL) was added EDC (886 mg, 4.6 mmol), HOAt (629 mg, 4.6 mmol) and 4-nitro-1,2-phenylenediamne (643 mg, 4.2 mmol). The resulting reaction mixture was stirred at room temperature for 16 h followed by quenching with aqueous NaHCO$_3$ and EtOAc. The layers were separated and the

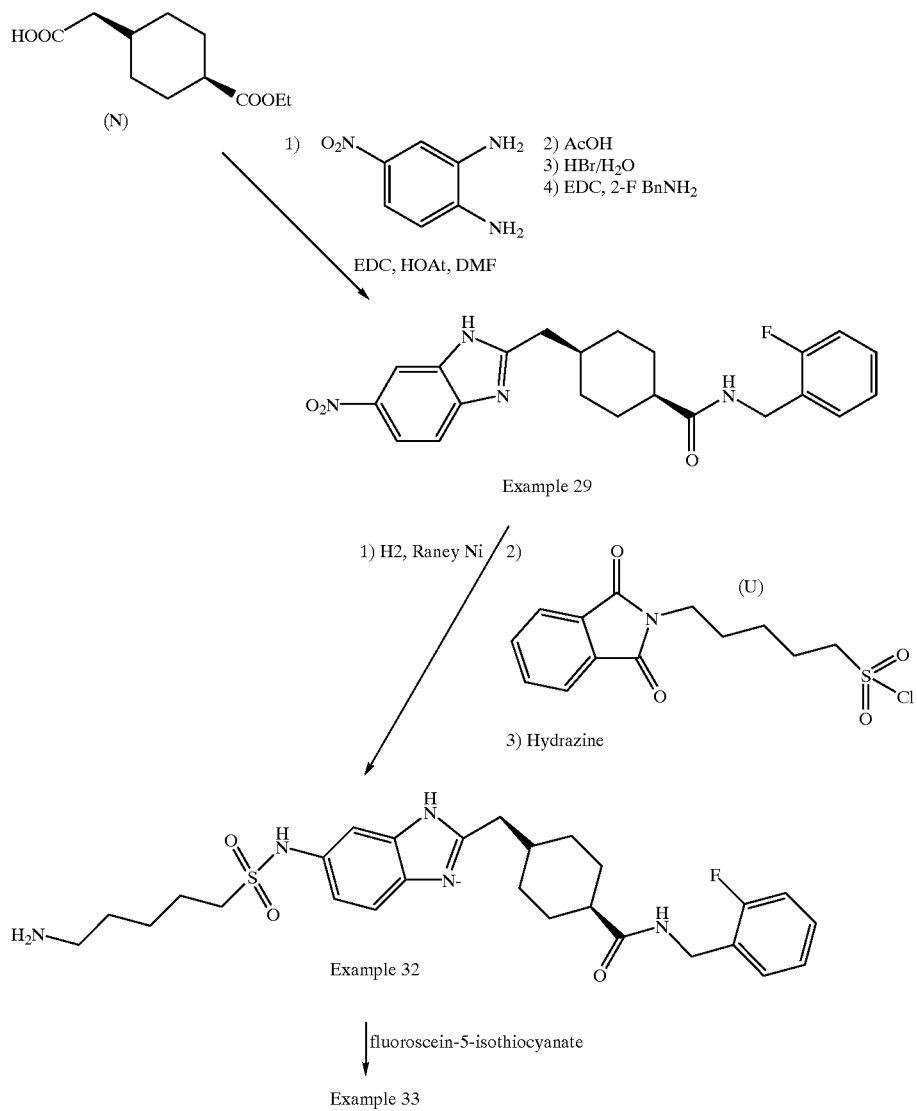

organic layer was washed twice with water, dried over Na₂SO₄, filtered and concentrated.

The resulting crude product was dissolved in acetic acid (5 mL) and heated to 130° C. for 1.5 h. The reaction mixture was cooled, concentrated and partitioned between aqueous NaHCO₃ and EtOAc, and the organic layer was dried over Na₂SO₄, filtered and concentrated. The resulting crude oil was used without purification: mass spectrum m/z 332 [(M+H)⁺; calcd for $C_{17}H_{22}N_3O_4$: 332].

Example 29

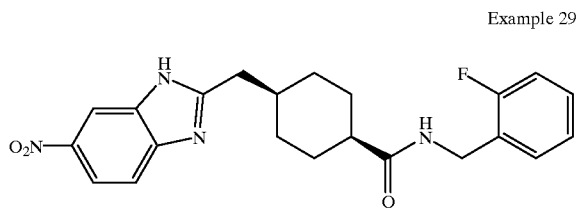

Example 29

Example 29 was prepared by the following procedure: Ester Compound (V) (450 mg, 1.36 mmol) was dissolved in BBr/H₂O (48%, 5 mL) and heated to 100° C. for 10 min. The reaction mixture was cooled, concentrated and the corresponding resulting acid was used without further purification: mass spectrum m(z 304 [(M+H)⁺; calcd for $C_{15}H_{18}N_3O_4$: 304].

To a solution of the above resulting acid (400 mg, 1.32 mmol), EDC (379 mg, 1.98 mmol) and HOAt (269 mg, 1.98 mmol) in anhydrous DMF (5 mL) was added 2-fluorobenzylamine (247 mg, 1.98 mmol) and the resulting reaction mixture was stirred for 2 h. The reaction mixture was partitioned between saturated aqueous NaHCO₃ and EtOAc and the organic layer was washed 2× with water. The EtOAc was dried with MgSO₄ and concentrate. The crude material was purified by reverse phase HPLC to give Example 29: ¹H NMR (300MH, CD₃OD) δ 8.61 (d, 1H), 8.42 (dd, 1H), 7.88 (d, 1H); 7.24 (m, 2H), 7.10 (m; 2H), 4.40 (s, 2H), 3.10 (d, 2H), 2.43 (m, 1H), 2.17 (m, 1H), 1.90 (m, 3H), 1.61 (m, 5H) ppm; mass spectrum m/z 411 [(M+H)⁺; calcd for $C_{22}H_{24}FN_4O_3$: 411].

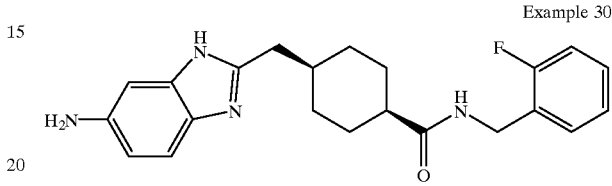

Example 30

Example 30 was prepared by the following procedure: To a solution of Example 29 (0.3 g, 0.73 mmol) in EtOH (4 mL) was added 10% Pd/C (0.05 g). The resulting reaction mixture was stirred under a balloon of hydrogen. After 2 h, the reaction mixture was filtered through celite, concentrated and the crude product purified by reverse phase HPLC to give Example 30: mass spectrum ml/z 381 [(M+H)⁺; calcd for $C_{22}H_{25}FN_4O$: 381].

Example 31

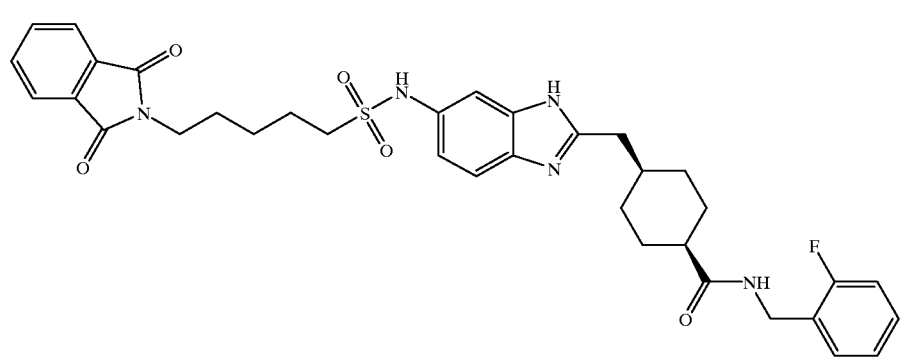

Example 31

Example 31 was prepared by the following procedure: To a Solution of Example 30 (15 mg, 0.04 mmol) in dichloromethane (1 mL) was added triethylamine (11 μL, 0.08 mmol) and sulfonyl chloride Compound (U) (12 mg, 0.04 mmol). The resulting mixture was stiffed at room temperature for 30 min, concentrated and purified by reverse phase HPLC to give Example 31: mass spectrum m/z 660 [(M+H)⁺; calcd for $C_{35}H_{39}FN_5O_5S$: 660].

Example 32

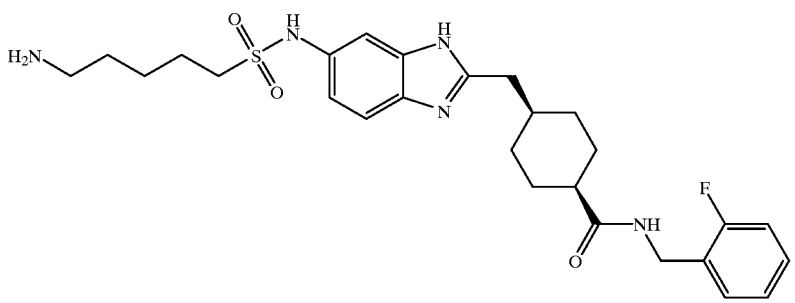

Example 32

Example 32 was prepared by the following procedure: To a room temperature solution of Example 31 (10 mg, 0.015 mmol) in EtOH (0.5 mL) was added hydrazine (4 μL, 0.15 mmol) and the reaction mixture was stirred for 2 h. The reaction mixture was concentrated and purified by reverse phase HPLC to give Example 32: mass spectrum m/z 530 [(M+H)+; calcd for $C_{27}H_{37}FN_5O_3S$: 530].

Example 33

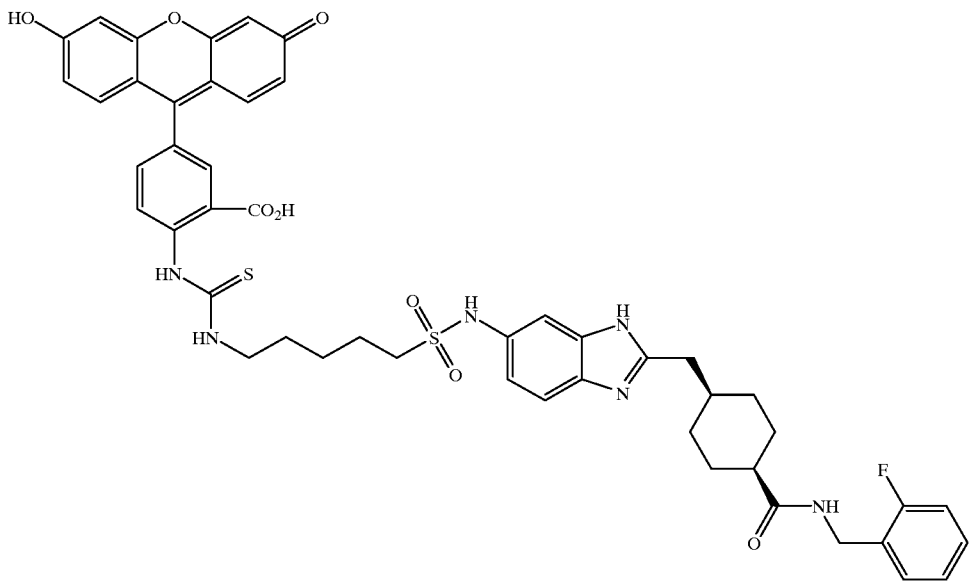

Example 33

Example 33 was prepared by the following procedure: To a room temperature solution of Example 32 (8 mg, 0015 mmol) in dichloromethane (1 mL) and MeOH (0.2 mL) was added fluoroscein-5-isothiocyanate (5 mg, 0.02 mmol) and triethylamine (10 μL). The resulting mixture was stirred for 30 min, concentrated, and purified by reverse phase HPLC to give Example 33: mass spectrum m/z 919 [(M+H)+; calcd for $C_{48}H_{48}FN_6O_8S_2$: 919].

Examples 34–106

Examples 34–106 were prepared by procedures similar to those described above.

In Table 1 below, the substituents are shown wherein $X_1$ corresponds to the NH group of the amide:

TABLE 1

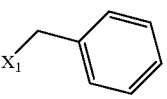

| Example | SUBSTITUENT | MS | NAME |
|---|---|---|---|
| 34 | 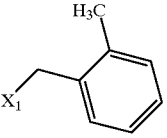 | 348 | cis-4-(1H-Benzoimidazol-2-ylmethyl)-cyclohexanecarboxyilic acid benzylamide |
| 35 | 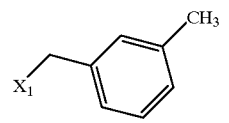 | 362 | cis-4-(1H-Benzoimidazol-2-ylmethyl)-cyclohexanecarboxyilic acid 2-methyl-benzylamide |
| 36 | 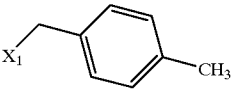 | 362 | cis-4-(1H-Benzoimidazol-2-ylmethyl)-cyclohexanecarboxyilic acid 3-methyl-benzylamide |
| 37 | 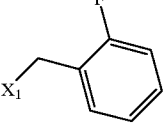 | 362 | cis-4-(1H-Benzoimidazol-2-ylmethyl)-cyclohexanecarboxyilic acid 4-methyl-benzylamide |
| 38 | 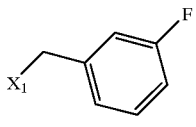 | 366 | cis-4-(1H-Benzoimidazol-2-ylmethyl)-cyclohexanecarboxyilic acid 2-fluoro-benzylamide |
| 39 | 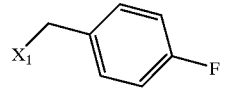 | 366 | cis-4-(1H-Benzoimidazol-2-ylmethyl)-cyclohexanecarboxyilic acid 3-fluoro-benzylamide |
| 40 | 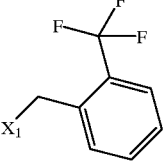 | 366 | cis-4-(1H-Benzoimidazol-2-ylmethyl)-cyclohexanecarboxyilic acid 4-fluoro-benzylamide |
| 41 |  | 416 | cis-4-(1H-Benzoimidazol-2-ylmethyl)-cyclohexanecarboxyilic acid 2-trifluoromethyl-benzylamide |

TABLE 1-continued

| Example | SUBSTITUENT | MS | NAME |
|---|---|---|---|
| 42 | 3-CF₃-benzyl | 416 | cis-4-(1H-Benzoimidazol-2-ylmethyl)-cyclohexanecarboxyilic acid 3-trifluoromethyl-benzylamide |
| 43 | 4-CF₃-benzyl | 416 | cis-4-(1H-Benzoimidazol-2-ylmethyl)-cyclohexanecarboxyilic acid 4-trifluoromethyl-benzylamide |
| 44 | 2-OCF₃-benzyl | 432 | cis-4-(1H-Benzoimidazol-2-ylmethyl)-cyclohexanecarboxyilic acid 2-trifluoromethoxy-benzylamide |
| 45 | 2-Cl-benzyl | 382 | cis-4-(1H-Benzoimidazol-2-ylmethyl)-cyclohexanecarboxyilic acid 2-chloro-benzylamide |
| 46 | 2-phenyl-benzyl | 424 | cis-4-(1H-Benzoimidazol-2-ylmethyl)-cyclohexanecarboxyilic acid 2-phenyl-benzylamide |
| 47 | 2-OCH₃-benzyl | 378 | cis-4-(1H-Benzoimidazol-2-ylmethyl)-cyclohexanecarboxyilic acid 2-methoxy-benzylamide |

TABLE 1-continued

| Example | SUBSTITUENT | MS | NAME |
|---------|-------------|-----|------|
| 48 | (2-methoxybenzyl) | 392 | cis-4-(1H-Benzoimidazol-2-ylmethyl)-cyclohexanecarboxyilic acid 2-methoxy-benzylamide |
| 49 | (2-fluoro-4-chlorobenzyl) | 400 | cis-4-(1H-Benzoimidazol-2-ylmethyl)-cyclohexanecarboxyilic acid 2-fluoro-4chloro-benzylamide |
| 50 | (2,6-dimethoxybenzyl) | 408 | cis-4-(1H-Benzoimidazol-2-ylmethyl)-cyclohexanecarboxyilic acid 2,6-dimethoxy-benzylamide |
| 51 | (2,4-dichlorobenzyl) | 417 | cis-4-(1H-Benzoimidazol-2-ylmethyl)-cyclohexanecarboxyilic acid 2,4-dichloro-benzylamide |
| 52 | (1-phenylethyl) | 362 | cis-4-(1H-Benzoimidazol-2-ylmethyl)-cyclohexanecarboxyilic acid (1-phenyl-ethyl)-amide |
| 53 | (4-methanesulfonylbenzyl) | 426 | cis-4-(1H-Benzoimidazol-2-ylmethyl)-cyclohexanecarboxyilic acid 4-methanesulfonyl-benzylamide |
| 54 | (2,6-dichlorobenzyl) | 417 | cis-4-(1H-Benzoimidazol-2-ylmethyl)-cyclohexanecarboxyilic acid 2,6-dichloro-benzylamide |

TABLE 1-continued

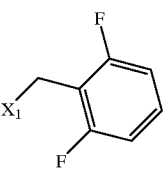

| Example | SUBSTITUENT | MS | NAME |
|---|---|---|---|
| 55 | (2,6-difluorobenzyl, X₁) | 384 | cis-4-(1H-Benzoimidazol-2-ylmethyl)-cyclohexanecarboxyilic acid 2,6-difluoro-benzylamide |

In Table 2 below, the substituents are shown wherein XI corresponds to the NH group of the amide:

TABLE 2

| Example | SUBSTITUENT | MASS | NAME |
|---|---|---|---|
| 56 | (2-methylbenzyl, X₁) | 362 | trans-4-(1H-Benzoimidazol-2-ylmethyl)-cyclohexanecarboxyilic acid 2-methyl-benzylamide |
| 57 | (3-methylbenzyl, X₁) | 362 | trans-4-(1H-Benzoimidazol-2-ylmethyl)-cyclohexanecarboxyilic acid 3-methyl-benzylamide |
| 58 | (4-methylbenzyl, X₁) | 362 | trans-4-(1H-Benzoimidazol-2-ylmethyl)-cyclohexanecarboxyilic acid 4-methyl-benzylamide |
| 59 | (2-fluorobenzyl, X₁) | 366 | trans-4-(1H-Benzoimidazol-2-ylmethyl)-cyclohexanecarboxyilic acid 2-fluoro-benzylamide |

TABLE 2-continued

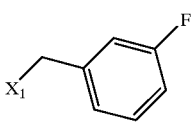

| Example | SUBSTITUENT | MASS | NAME |
|---|---|---|---|
| 60 | 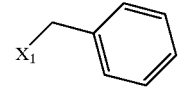 | 366 | trans-4-(1H-Benzoimidazol-2-ylmethyl)-cyclohexanecarboxyilic acid 3-fluoro-benzylamide |
| 61 | 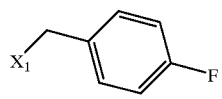 | 348 | trans-4-(1H-Benzoimidazol-2-ylmethyl)-cyclohexanecarboxyilic acid benzylamide |
| 62 | 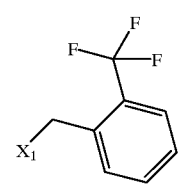 | 366 | trans-4-(1H-Benzoimidazol-2-ylmethyl)-cyclohexanecarboxyilic acid 4-fluoro-benzylamide |
| 63 | 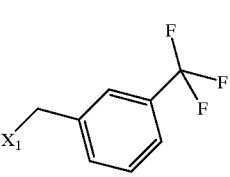 | 416 | trans-4-(1H-Benzoimidazol-2-ylmethyl)-cyclohexanecarboxyilic acid 2-trifluoromethyl-benzylamide |
| 64 | 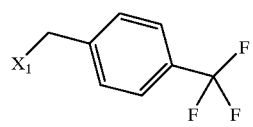 | 416 | trans-4-(1H-Benzoimidazol-2-ylmethyl)-cyclohexanecarboxyilic acid 3-trifluoromethyl-benzylamide |
| 65 |  | 416 | trans-4-(1H-Benzoimidazol-2-ylmethyl)-cyclohexanecarboxyilic acid 4-trifluoromethyl-benzylamide |

In Table 3 below, the substituents are shown wherein XI corresponds to the NH group of the amide:

TABLE 3

[Structure: trans-4-(1H-benzoimidazol-2-ylamino)-cyclohexanecarboxylic acid amide with variable substituent on amide NH]

| Example | SUBSTITUENT | MS | NAME |
|---|---|---|---|
| 66 | X₁–CH₂–phenyl | 349 | trans-4-(1H-Benzoimidazol-2-ylamino)-cyclohexanecarboxyilic acid benzylamide |
| 67 | X₁–phenyl | 335 | trans-4-(1H-Benzoimidazol-2-ylamino)-cyclohexanecarboxyilic acid phenylamide |
| 68 | X₁–CH₂–(2-OCH₃-phenyl) | 379 | trans-4-(1H-Benzoimidazol-2-ylamino)-cyclohexanecarboxyilic acid 2-methoxy-benzylamide |
| 69 | X₁–CH₂–(naphthalen-1-yl) | 399 | trans-4-(1H-Benzoimidazol-2-ylamino)-cyclohexanecarboxylic acid (naphthalen-1-ylmethyl)-amide |
| 70 | X₁–CH₂–(4-(1,2,3-thiadiazol-4-yl)phenyl) | 433 | trans-4-(1H-Benzoimidazol-2-ylamino)-cyclohexanecarboxylic acid 4-(1,2,3)thiadiazol-4-yl-benzylamide |
| 71 | X₁–indan-2-yl | 375 | trans-4-(1H-Benzoimidazol-2-ylamino)-cyclohexanecarboxylic acid indan-2-ylamide |
| 72 | X₁–CH₂–(2-methylphenyl) | 363 | trans-4-(1H-Benzoimidazol-2-ylamino)-cyclohexanecarboxyilic acid 2-methyl-benzylamide |
| 73 | X₁–CH₂–(3-methylphenyl) | 363 | trans-4-(1H-Benzoimidazol-2-ylamino)-cyclohexanecarboxyilic acid 3-methyl-benzylamide |

TABLE 3-continued

| Example | SUBSTITUENT | MS | NAME |
|---|---|---|---|
| 74 | X₁—C₆H₄—CH₃ (4-methyl) | 363 | trans-4-(1H-Benzoimidazol-2-ylamino)-cyclohexanecarboxyilic acid 4-methyl-benzylamide |
| 75 | X₁—C₆H₄—Cl (2-chloro) | 383 | trans-4-(1H-Benzoimidazol-2-ylamino)-cyclohexanecarboxyilic acid 2-chloro-benzylamide |
| 76 | X₁—C₆H₄—Cl (3-chloro) | 383 | trans-4-(1H-Benzoimidazol-2-ylamino)-cyclohexanecarboxyilic acid 3-chloro-benzylamide |
| 77 | X₁—C₆H₄—Cl (4-chloro) | 383 | trans-4-(1H-Benzoimidazol-2-ylamino)-cyclohexanecarboxyilic acid 4-chloro-benzylamide |
| 78 | X₁—C₆H₄—F (2-fluoro) | 367 | trans-4-(1H-Benzoimidazol-2-ylamino)-cyclohexanecarboxyilic acid 2-fluoro-benzylamide |
| 79 | X₁—C₆H₄—F (3-fluoro) | 367 | trans-4-(1H-Benzoimidazol-2-ylamino)-cyclohexanecarboxyilic acid 3-fluoro-benzylamide |
| 80 | X₁—C₆H₄—F (4-fluoro) | 367 | trans-4-(1H-Benzoimidazol-2-ylamino)-cyclohexanecarboxyilic acid 4-fluoro-benzylamide |

TABLE 3-continued

| Example | SUBSTITUENT | MS | NAME |
|---------|-------------|-----|------|
| 81 | X₁—CH₂—C₆H₄—O—CH₃ (3-methoxy) | 379 | trans-4-(1H-Benzoimidazol-2-ylamino)-cyclohexanecarboxyilic acid 3-methoxy-benzylamide |
| 82 | X₁—CH₂—C₆H₄—O—CH₃ (4-methoxy) | 379 | trans-4-(1H-Benzoimidazol-2-ylamino)-cyclohexanecarboxyilic acid 4-methoxy-benzylamide |
| 83 | X₁—CH₂—C₆H₄—CF₃ (2-) | 417 | trans-4-(1H-Benzoimidazol-2-ylamino)-cyclohexanecarboxyilic acid 2-trifluoromethyl-benzylamide |
| 84 | X₁—CH₂—C₆H₄—CF₃ (3-) | 417 | trans-4-(1H-Benzoimidazol-2-ylamino)-cyclohexanecarboxyilic acid 3-trifluoromethyl-benzylamide |
| 85 | X₁—CH₂—C₆H₄—CF₃ (4-) | 417 | trans-4-(1H-Benzoimidazol-2-ylamino)-cyclohexanecarboxyilic acid 4-trifluoromethyl-benzylamide |
| 86 | X₁—CH₂—C₆H₄—OCF₃ (2-) | 433 | trans-4-(1H-Benzoimidazol-2-ylamino)-cyclohexanecarboxyilic acid 2-trifluoromethoxy-benzylamide |
| 87 | X₁—CH₂—C₆H₄—OCF₃ (3-) | 433 | trans-4-(1H-Benzoimidazol-2-ylamino)-cyclohexanecarboxyilic acid 3-trifluoromethoxy-benzylamide |

TABLE 3-continued

| Example | SUBSTITUENT | MS | NAME |
|---|---|---|---|
| 88 | X₁—CH₂—C₆H₄—OCF₃ (4-trifluoromethoxybenzyl) | 433 | trans-4-(1H-Benzoimidazol-2-ylamino)-cyclohexanecarboxyilic acid 4-trifluoromethoxy-benzylamide |
| 89 | X₁—CH₂—(3,5-dimethylphenyl) | 377 | trans-4-(1H-Benzoimidazol-2-ylamino)-cyclohexanecarboxyilic acid 3,5-dimethyl-benzylamide |
| 90 | X₁—CH₂—(benzo[1,3]dioxol-5-yl) | 393 | trans-4-(1H-Benzoimidazol-2-ylamino)-cyclohexanecarboxyilic acid (benzo(1,3)dioxol-5-ylmethyl)-amide |
| 91 | X₁—CH₂—(2-methoxyphenyl) | 379 | trans-4-(1H-Benzoimidazol-2-ylamino)-cyclohexanecarboxyilic acid 2-methoxy-benzylamide |
| 92 | X₁—CH(CH₃)—C₆H₅ | 363 | trans-4-(1H-Benzoimidazol-2-ylamino)-cyclohexanecarboxyilic acid (1-phenyl-ethyl)-amide |
| 93 | X₁—CH₂CH₂—C₆H₅ | 363 | trans-4-(1H-Benzoimidazol-2-ylamino)-cyclohexanecarboxyilic acid phenethyl-amide |
| 94 | X₁—CH₂—(3,4-difluorophenyl) | 385 | trans-4-(1H-Benzoimidazol-2-ylamino)-cyclohexanecarboxyilic acid 3,4-difluoro-benzylamide |

TABLE 3-continued

| Example | SUBSTITUENT | MS | NAME |
|---------|-------------|-----|------|
| 95 | (2-methoxy, with X₁-CH₂ at ortho position) | 425 | trans-4-(1H-Benzoimidazol-2-ylamino)-cyclohexanecarboxyilic acid 3-phenyl-benzylamide |

In Table 4 below, the substituents are shown wherein XI corresponds to the NH group of the amide:

TABLE 4

| Example | SUBSTITUENT | MS | NAME |
|---------|-------------|-----|------|
| 96 | X₁—CH₂-phenyl | 349 | cis-4-(1H-Benzoimidazol-2-ylamino)-cyclohexanecarboxyilic acid benzylamide |
| 97 | X₁-phenyl | 335 | cis-4-(1H-Benzoimidazol-2-ylamino)-cyclohexanecarboxyilic acid phenylamide |
| 98 | X₁—CH₂-(2-methoxyphenyl) | 379 | cis-4-(1H-Benzoimidazol-2-ylamino)-cyclohexanecarboxyilic acid 2-methoxy-benzylamide |
| 99 | X₁—CH₂-(naphthalen-1-yl) | 399 | cis-4-(1H-Benzoimidazol-2-ylamino)-cyclohexanecarboxyilic acid (naphthalen-1-ylmethyl)-amide |

…

TABLE 4-continued

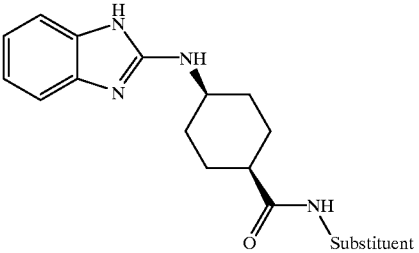

| | Substituent | | |
|---|---|---|---|
| 100 | 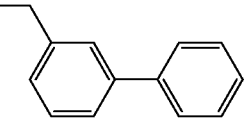 | 425 | cis-4-(1H-Benzoimidazol-2-ylamino)-cyclohexanecarboxyilic acid 3-phenyl-benzylamide |

Examples 102–106

| Example | Structure | MASS | NAME |
|---|---|---|---|
| 101 | 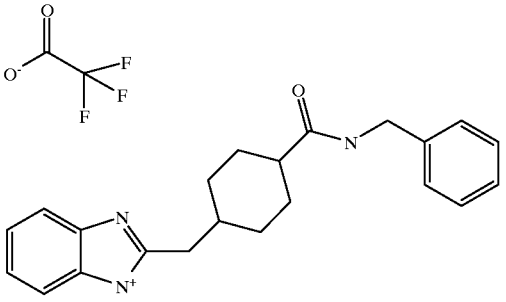 | 348 | 4-(1H-Benzoimidazol-2-ylmethyl)-cyclohexanecarboxyilic acid benzylamide |
| 102 | 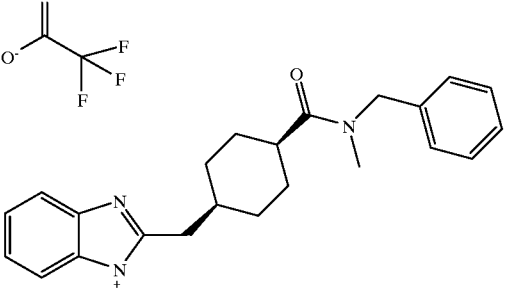 | 362 | 4-(1H-Benzoimidazol-2-ylamino)-cyclohexanecarboxylic acid benzyl-methyl-amide |
| 103 | 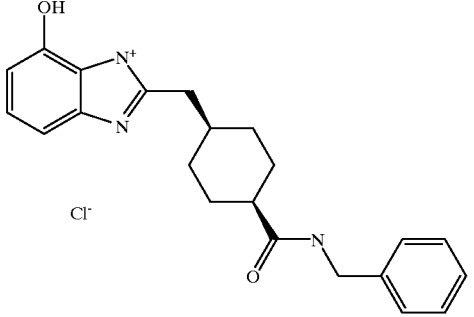 | 364 | cis-4-(3-Hydroxy-1H-benzoimidazol-2 ylmethyl)-cyclohexanecarboxyilic acid benzylamide |

-continued

| Example | Structure | MASS | NAME |
|---|---|---|---|
| 104 | 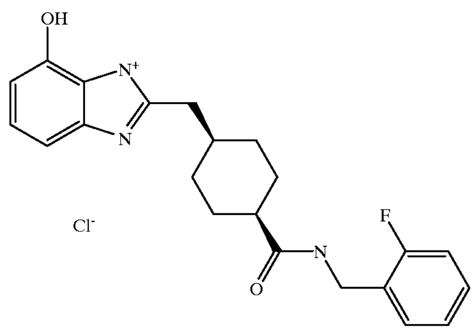 | 382 | cis-4-(3-Hydroxy-1H-benzoimidazol-2 ylmethyl)-cyclohexanecarboxyilic acid 2-fluoro-benzylamide |
| 105 | 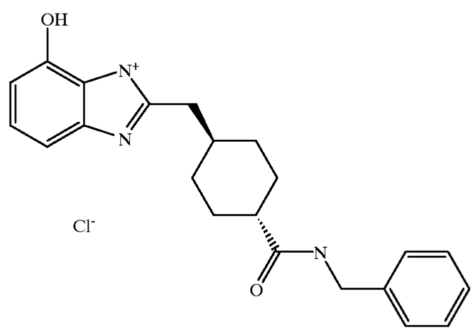 | 364 | trans-4-(3-Hydroxy-1H-benzoimidazol-2-ylmethyl)-cyclohexanecarboxyilic acid benzylamide |
| 106 | 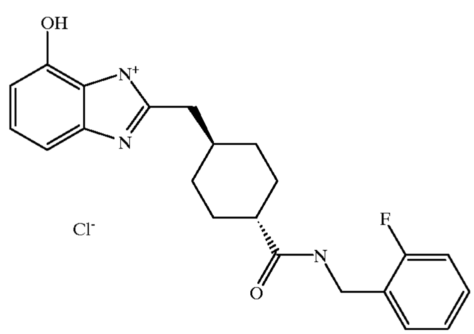 | 382 | trans-4-(3-Hydroxy-1H-benzoimidazol-2-ylmethyl)-cyclohexanecarboxyilic acid 2-fluoro-benzylamide |

What is claimed is:

1. A compound having the formula:

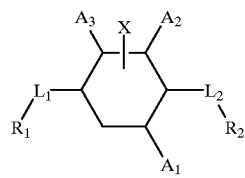

or a pharmaceutically acceptable salt thereof, wherein
$R_1$ is 2-benzimidazole, optionally substituted with fluoro, amino, or hydroxy;
$R_2$ is phenyl, optionally substituted with one to five substituents, each substituent independently being chloro, fluoro, bromo, $C_1$–$C_4$alkyl, trifluoromethyl, hydroxy, or carboxy;
$L_1$ and $L_2$ are independently $C_1$–$C_4$alkyl, $C_1$–$C_4$alkenyl, $C_1$–$C_4$alkynyl, $C_1$–$C_4$alkoxy, amino, amino$C_1$–$C_4$alkyl, hydroxy$C_1$–$C_4$alkyl, carbonyl, cyclo$C_3$–$C_6$alkyl or aminocarbonyl;

$A_1$, $A_2$, and $A_3$ are each hydrogen or i) $A_1$ and $A_2$ form a two carbon bridge or ii) $A_1$ and $A_3$ form a two carbon bridge; and optionally substituted with X, wherein X is hydroxy, amino, $C_1$–$C_4$alkylamino, di($C_1$–$C_4$)alkylamino, $C_1$–$C_4$alkyl, ester, carbamate, carbonate, or ether.

2. The compound according to claim 1, wherein $R_1$ is 2-benzimidazole.

3. The compound according to claim 1, wherein said compound is

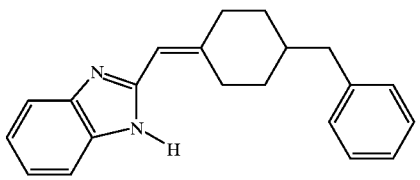

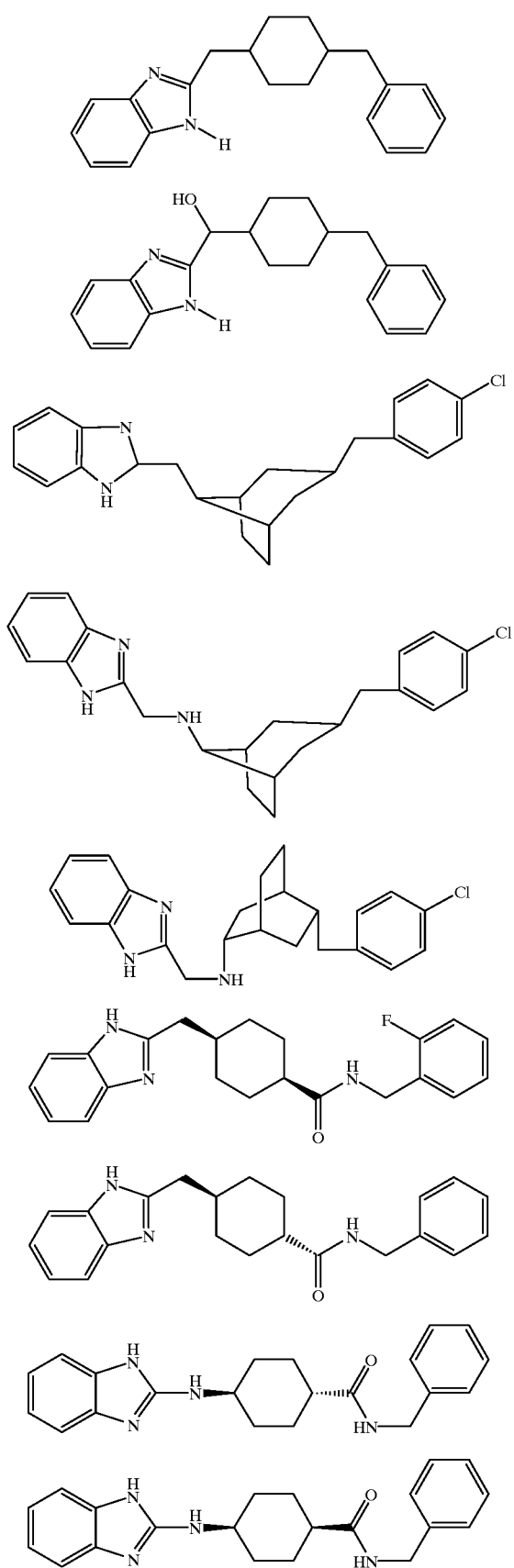

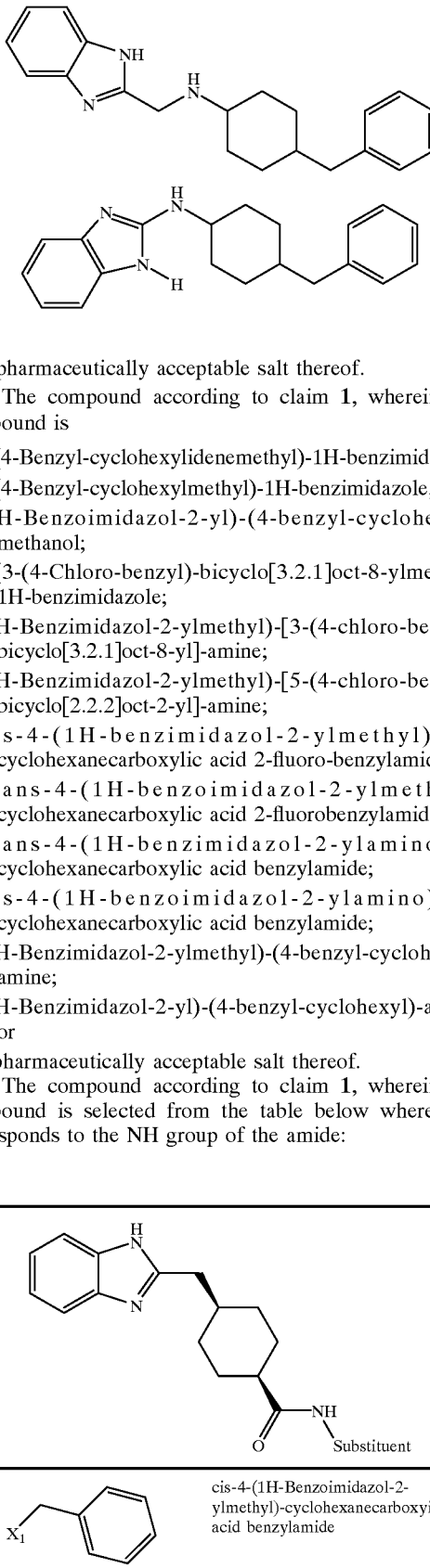

or a pharmaceutically acceptable salt thereof.

4. The compound according to claim 1, wherein said compound is 2-(4-Benzyl-cyclohexylidenemethyl)-1H-benzimidazole;

2-(4-Benzyl-cyclohexylmethyl)-1H-benzimidazole;

(1H-Benzoimidazol-2-yl)-(4-benzyl-cyclohexyl)-methanol;

2-[3-(4-Chloro-benzyl)-bicyclo[3.2.1]oct-8-ylmethyl]-1H-benzimidazole;

(1H-Benzimidazol-2-ylmethyl)-[3-(4-chloro-benzyl)-bicyclo[3.2.1]oct-8-yl]-amine;

(1H-Benzimidazol-2-ylmethyl)-[5-(4-chloro-benzyl)-bicyclo[2.2.2]oct-2-yl]-amine;

Cis-4-(1H-benzimidazol-2-ylmethyl)-cyclohexanecarboxylic acid 2-fluoro-benzylamide;

Trans-4-(1H-benzoimidazol-2-ylmethyl)-cyclohexanecarboxylic acid 2-fluorobenzylamide;

Trans-4-(1H-benzoimidazol-2-ylamino)-cyclohexanecarboxylic acid benzylamide;

Cis-4-(1H-benzoimidazol-2-ylamino)-cyclohexanecarboxylic acid benzylamide;

(1H-Benzimidazol-2-ylmethyl)-(4-benzyl-cyclohexyl)-amine;

(1H-Benzimidazol-2-yl)-(4-benzyl-cyclohexyl)-amine; or a pharmaceutically acceptable salt thereof.

5. The compound according to claim 1, wherein said compound is selected from the table below wherein X1 corresponds to the NH group of the amide:

|  |  |
|---|---|
|  | cis-4-(1H-Benzoimidazol-2-ylmethyl)-cyclohexanecarboxyilic acid benzylamide |

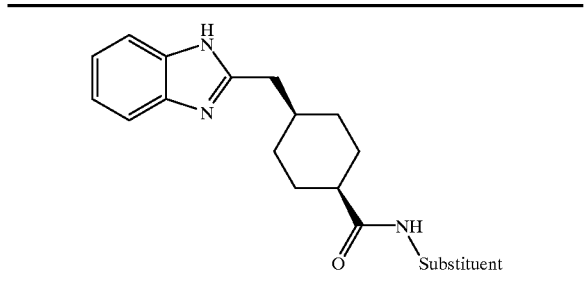

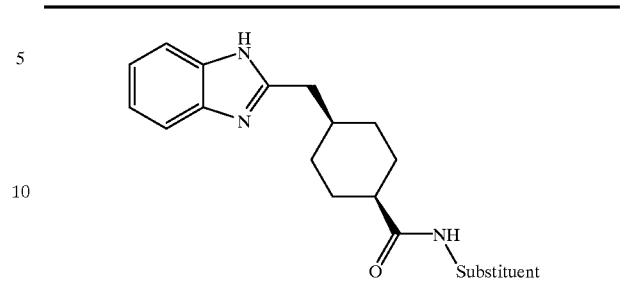

| Structure | Name |
|---|---|
| 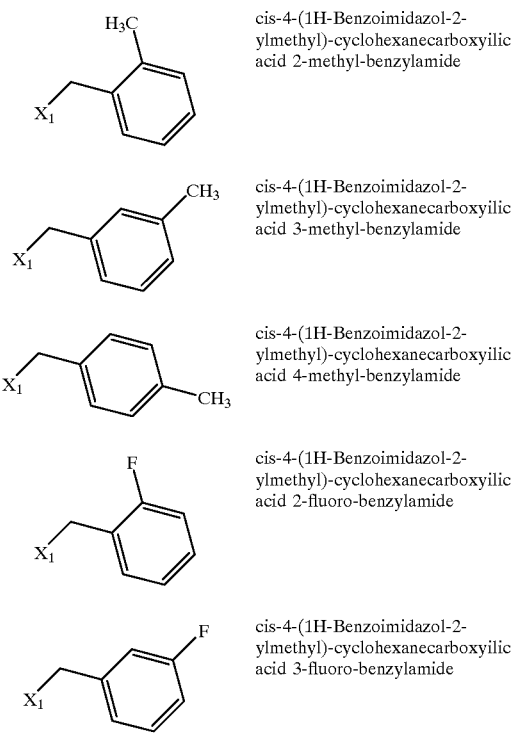 | cis-4-(1H-Benzoimidazol-2-ylmethyl)-cyclohexanecarboxyilic acid 2-methyl-benzylamide |
| | cis-4-(1H-Benzoimidazol-2-ylmethyl)-cyclohexanecarboxyilic acid 3-methyl-benzylamide |
| | cis-4-(1H-Benzoimidazol-2-ylmethyl)-cyclohexanecarboxyilic acid 4-methyl-benzylamide |
| | cis-4-(1H-Benzoimidazol-2-ylmethyl)-cyclohexanecarboxyilic acid 2-fluoro-benzylamide |
| | cis-4-(1H-Benzoimidazol-2-ylmethyl)-cyclohexanecarboxyilic acid 3-fluoro-benzylamide |
| | cis-4-(1H-Benzoimidazol-2-ylmethyl)-cyclohexanecarboxyilic acid 4-fluoro-benzylamide |
| | cis-4-(1H-Benzoimidazol-2-ylmethyl)-cyclohexanecarboxyilic acid 2-trifluoromethyl-benzylamide |
| | cis-4-(1H-Benzoimidazol-2-ylmethyl)-cyclohexanecarboxyilic acid 3-trifluoromethyl-benzylamide |
| | cis-4-(1H-Benzoimidazol-2-ylmethyl)-cyclohexanecarboxyilic acid 4-trifluoromethyl-benzylamide |

| Structure | Name |
|---|---|
| 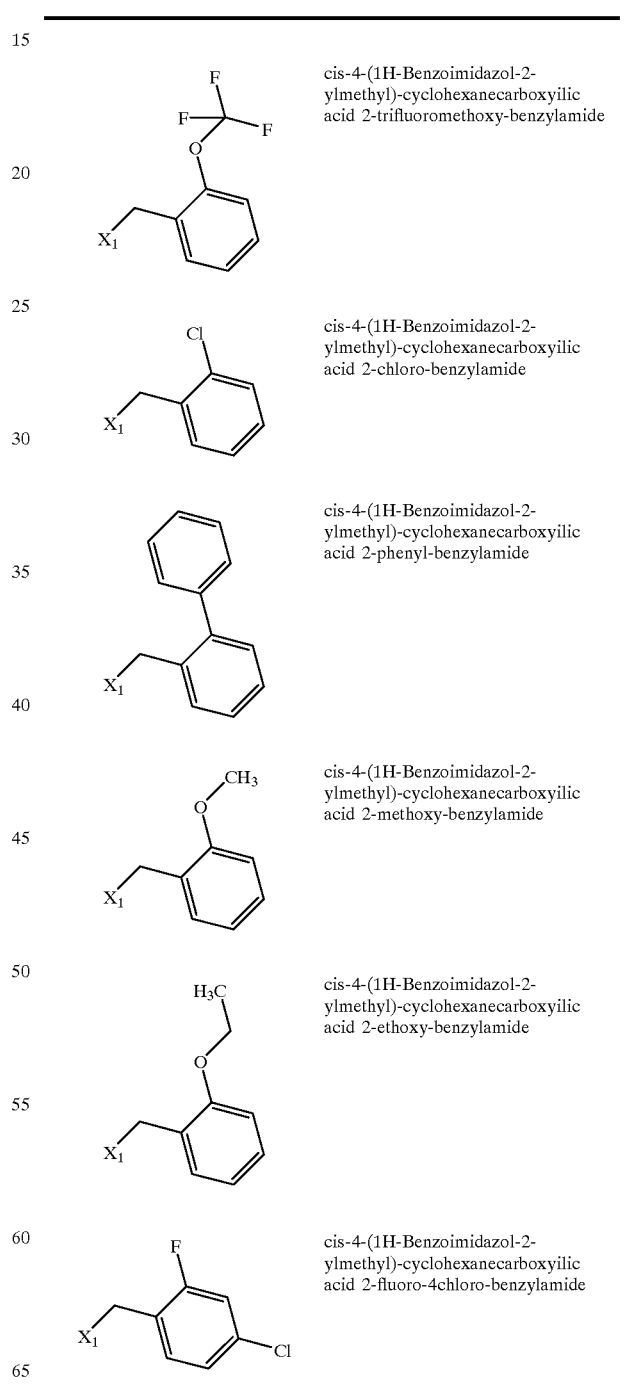 | cis-4-(1H-Benzoimidazol-2-ylmethyl)-cyclohexanecarboxyilic acid 2-trifluoromethoxy-benzylamide |
| | cis-4-(1H-Benzoimidazol-2-ylmethyl)-cyclohexanecarboxyilic acid 2-chloro-benzylamide |
| | cis-4-(1H-Benzoimidazol-2-ylmethyl)-cyclohexanecarboxyilic acid 2-phenyl-benzylamide |
| | cis-4-(1H-Benzoimidazol-2-ylmethyl)-cyclohexanecarboxyilic acid 2-methoxy-benzylamide |
| | cis-4-(1H-Benzoimidazol-2-ylmethyl)-cyclohexanecarboxyilic acid 2-ethoxy-benzylamide |
| | cis-4-(1H-Benzoimidazol-2-ylmethyl)-cyclohexanecarboxyilic acid 2-fluoro-4chloro-benzylamide |

| Structure | Name |
|---|---|
| cis-isomer with Substituent on amide | |
| 2,6-dimethoxybenzyl | cis-4-(1H-Benzoimidazol-2-ylmethyl)-cyclohexanecarboxyilic acid 2,6-dimethoxy-benzylamide |
| 2,4-dichlorobenzyl | cis-4-(1H-Benzoimidazol-2-ylmethyl)-cyclohexanecarboxyilic acid 2,4-dichloro-benzylamide |
| 1-phenylethyl | cis-4-(1H-Benzoimidazol-2-ylmethyl)-cyclohexanecarboxylic acid (1-phenyl-ethyl)-amide |
| 4-methanesulfonylbenzyl | cis-4-(1H-Benzoimidazol-2-ylmethyl)-cyclohexanecarboxyilic acid 4-methanesulfonyl-benzylamide |
| 2,6-dichlorobenzyl | cis-4-(1H-Benzoimidazol-2-ylmethyl)-cyclohexanecarboxyilic acid 2,6-dichloro-benzylamide |
| 2,6-difluorobenzyl | cis-4-(1H-Benzoimidazol-2-ylmethyl)-cyclohexanecarboxyilic acid 2,6-difluoro-benzylamide | or a pharmaceutically acceptable salt thereof.

6. The compound according to claim 1, wherein said compound is selected from the table below wherein $X_1$ corresponds to the NH group of the amide:

| Structure | Name |
|---|---|
| trans-isomer with Substituent on amide | |
| 2-methylbenzyl | trans-4-(1H-Benzoimidazol-2-ylmethyl)-cyclohexanecarboxyilic acid 2-methyl-benzylamide |
| 3-methylbenzyl | trans-4-(1H-Benzoimidazol-2-ylmethyl)-cyclohexanecarboxyilic acid 3-methyl-benzylamide |
| 4-methylbenzyl | trans-4-(1H-Benzoimidazol-2-ylmethyl)-cyclohexanecarboxyilic acid 4-methyl-benzylamide |
| 2-fluorobenzyl | trans-4-(1H-Benzoimidazol-2-ylmethyl)-cyclohexanecarboxyilic acid 2-fluoro-benzylamide |
| 3-fluorobenzyl | trans-4-(1H-Benzoimidazol-2-ylmethyl)-cyclohexanecarboxyilic acid 3-fluoro-benzylamide |
| benzyl | trans-4-(1H-Benzoimidazol-2-ylmethyl)-cyclohexanecarboxyilic acid benzylamide |
| 4-fluorobenzyl | trans-4-(1H-Benzoimidazol-2-ylmethyl)-cyclohexanecarboxyilic acid 4-fluoro-benzylamide |
| 2-trifluoromethylbenzyl | trans-4-(1H-Benzoimidazol-2-ylmethyl)-cyclohexanecarboxyilic acid 2-trifluoromethyl-benzylamide |
| 3-trifluoromethylbenzyl | trans-4-(1H-Benzoimidazol-2-ylmethyl)-cyclohexanecarboxyilic acid 3-trifluoromethyl-benzylamide |

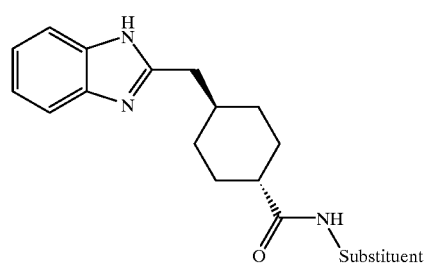

| | |
|---|---|
| 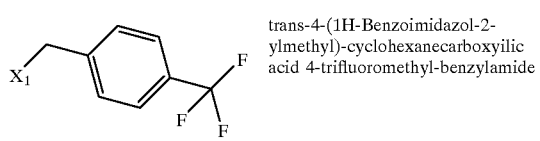 | trans-4-(1H-Benzoimidazol-2-ylmethyl)-cyclohexanecarboxyilic acid 4-trifluoromethyl-benzylamide | or a pharmaceutically acceptable salt thereof.

7. The compound according to claim 1, wherein said compound is selected from the table below wherein $X_1$ corresponds to the NH group of the amide:

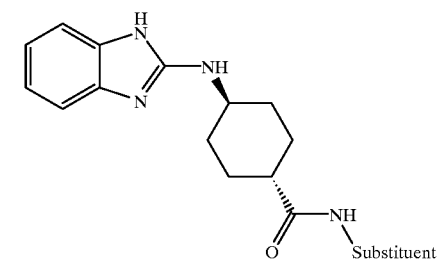

| | |
|---|---|
| 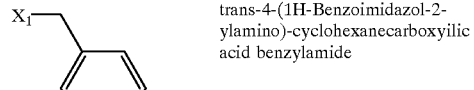 | trans-4-(1H-Benzoimidazol-2-ylamino)-cyclohexanecarboxyilic acid benzylamide |
| 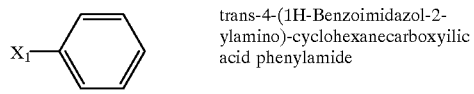 | trans-4-(1H-Benzoimidazol-2-ylamino)-cyclohexanecarboxyilic acid phenylamide |
| 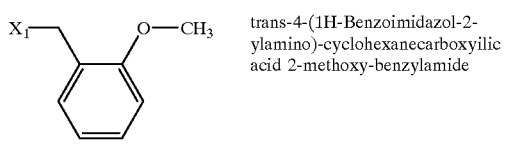 | trans-4-(1H-Benzoimidazol-2-ylamino)-cyclohexanecarboxyilic acid 2-methoxy-benzylamide |
| 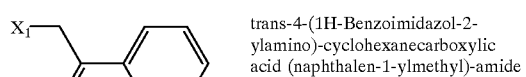 | trans-4-(1H-Benzoimidazol-2-ylamino)-cyclohexanecarboxylic acid (naphthalen-1-ylmethyl)-amide |
| 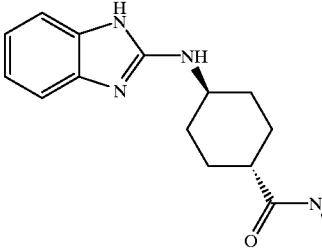 | trans-4-(1H-Benzoimidazol-2-ylamino)-cyclohexanecarboxylic acid 4-(1,2,3)thiadiazol-4-yl-benzylamide |
| 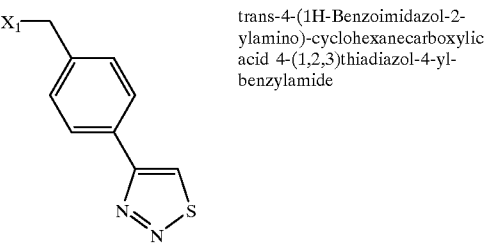 | |
| 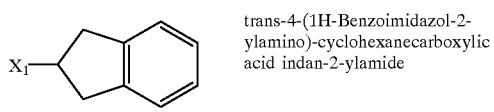 | trans-4-(1H-Benzoimidazol-2-ylamino)-cyclohexanecarboxyilic acid indan-2-ylamide |
| 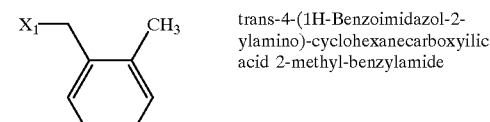 | trans-4-(1H-Benzoimidazol-2-ylamino)-cyclohexanecarboxyilic acid 2-methyl-benzylamide |
| 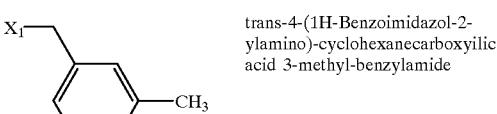 | trans-4-(1H-Benzoimidazol-2-ylamino)-cyclohexanecarboxyilic acid 3-methyl-benzylamide |
| 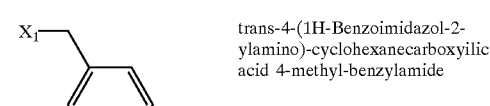 | trans-4-(1H-Benzoimidazol-2-ylamino)-cyclohexanecarboxyilic acid 4-methyl-benzylamide |
| 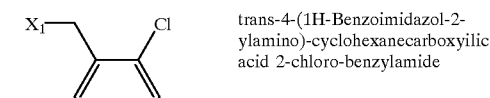 | trans-4-(1H-Benzoimidazol-2-ylamino)-cyclohexanecarboxyilic acid 2-chloro-benzylamide |
| 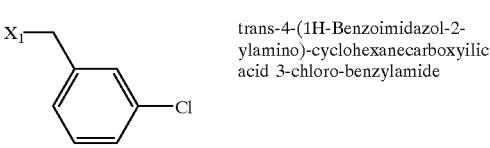 | trans-4-(1H-Benzoimidazol-2-ylamino)-cyclohexanecarboxyilic acid 3-chloro-benzylamide |
| 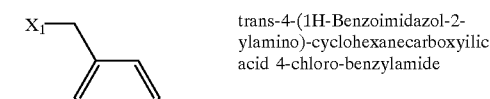 | trans-4-(1H-Benzoimidazol-2-ylamino)-cyclohexanecarboxyilic acid 4-chloro-benzylamide |

-continued

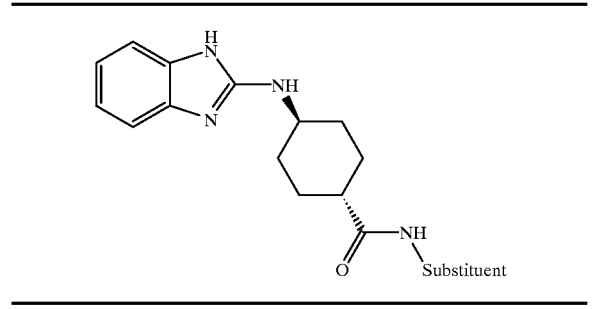

| Substituent | Name |
|---|---|
| 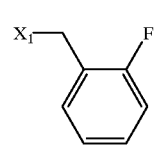 | trans-4-(1H-Benzoimidazol-2-ylamino)-cyclohexanecarboxyilic acid 2-fluoro-benzylamide |
| 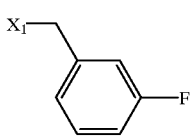 | trans-4-(1H-Benzoimidazol-2-ylamino)-cyclohexanecarboxyilic acid 3-fluoro-benzylamide |
| 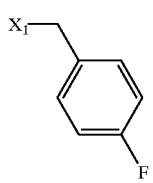 | trans-4-(1H-Benzoimidazol-2-ylamino)-cyclohexanecarboxyilic acid 4-fluoro-benzylamide |
| 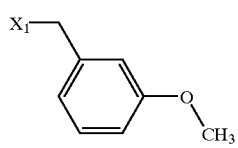 | trans-4-(1H-Benzoimidazol-2-ylamino)-cyclohexanecarboxyilic acid 3-methoxy-benzylamide |
| 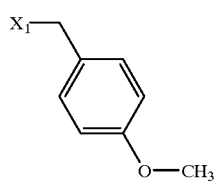 | trans-4-(1H-Benzoimidazol-2-ylamino)-cyclohexanecarboxyilic acid 4-methoxy-benzylamide |
| 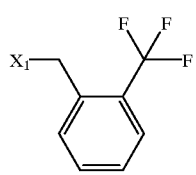 | trans-4-(1H-Benzoimidazol-2-ylamino)-cyclohexanecarboxyilic acid 2-trifluoromethyl-benzylamide |
| 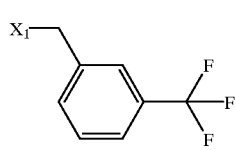 | trans-4-(1H-Benzoimidazol-2-ylamino)-cyclohexanecarboxyilic acid 3-trifluoromethyl-benzylamide |

-continued

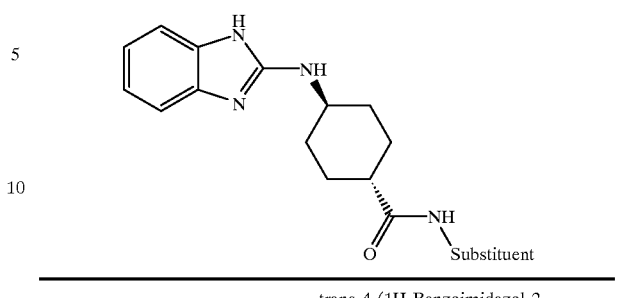

| Substituent | Name |
|---|---|
| 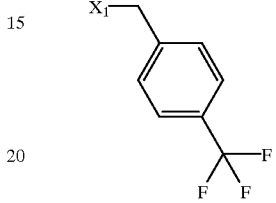 | trans-4-(1H-Benzoimidazol-2-ylamino)-cyclohexanecarboxyilic acid 4-trifluoromethyl-benzylamide |
| 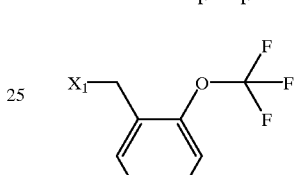 | trans-4-(1H-Benzoimidazol-2-ylamino)-cyclohexanecarboxyilic acid 2-trifluoromethoxy-benzylamide |
| 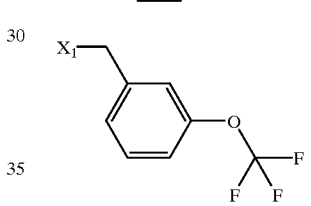 | trans-4-(1H-Benzoimidazol-2-ylamino)-cyclohexanecarboxyilic acid 3-trifluoromethoxy-benzylamide |
| 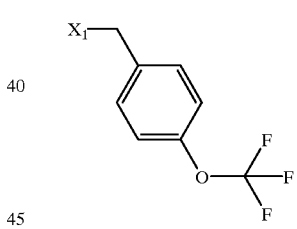 | trans-4-(1H-Benzoimidazol-2-ylamino)-cyclohexanecarboxyilic acid 4-trifluoromethoxy-benzylamide |
| 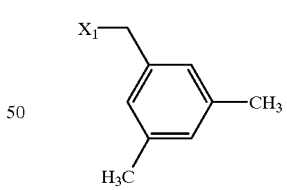 | trans-4-(1H-Benzoimidazol-2-ylamino)-cyclohexanecarboxyilic acid 3,5-dimethyl-benzylamide |
| 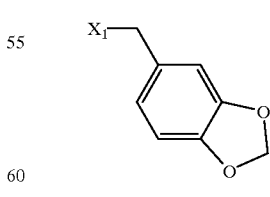 | trans-4-(1H-Benzoimidazol-2-ylamino)-cyclohexanecarboxylic acid (benzo(1,3)dioxol-5-ylmethyl)-amide |
| 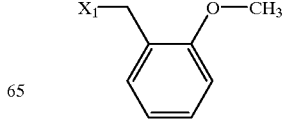 | trans-4-(1H-Benzoimidazol-2-ylamino)-cyclohexanecarboxyilic acid 2-methoxy-benzylamide |

-continued

| | trans-4-(1H-Benzoimidazol-2-ylamino)-cyclohexanecarboxylic acid (1-phenyl-ethyl)-amide |
| | trans-4-(1H-Benzoimidazol-2-ylamino)-cyclohexanecarboxylic acid phenethyl-amide |
| | trans-4-(1H-Benzoimidazol-2-ylamino)-cyclohexanecarboxyilic acid 3,4-difluoro-benzylamide |
| | trans-4-(1H-Benzoimidazol-2-ylamino)-cyclohexanecarboxyilic acid 3-phenyl-benzylamide | or a pharmaceutically acceptable salt thereof.

8. The compound according to claim 1, wherein said compound is selected from the table below wherein $X_1$ corresponds to the NH group of the amide:

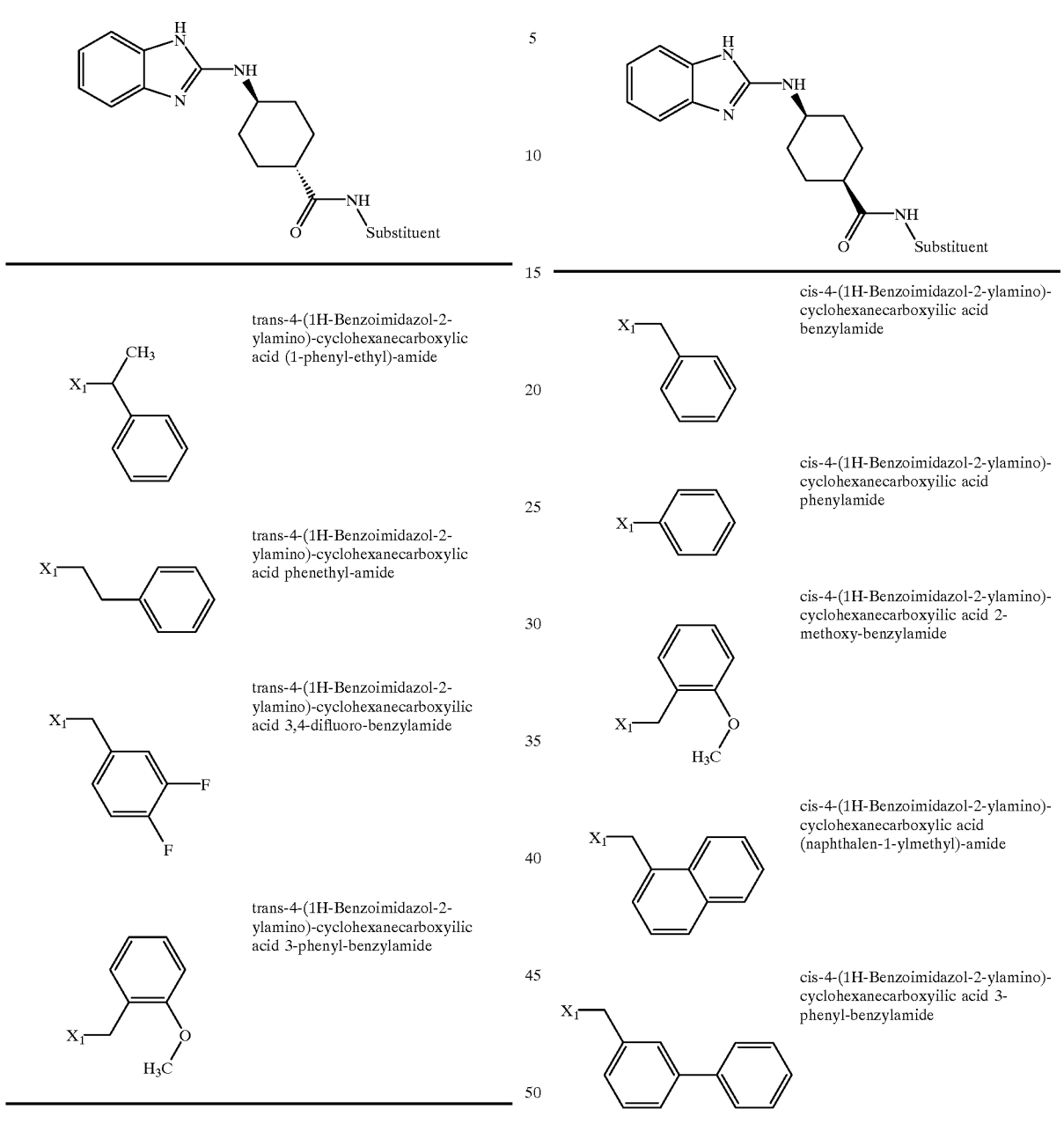

| | cis-4-(1H-Benzoimidazol-2-ylamino)-cyclohexanecarboxyilic acid benzylamide |
| | cis-4-(1H-Benzoimidazol-2-ylamino)-cyclohexanecarboxyilic acid phenylamide |
| | cis-4-(1H-Benzoimidazol-2-ylamino)-cyclohexanecarboxylic acid 2-methoxy-benzylamide |
| | cis-4-(1H-Benzoimidazol-2-ylamino)-cyclohexanecarboxylic acid (naphthalen-1-ylmethyl)-amide |
| | cis-4-(1H-Benzoimidazol-2-ylamino)-cyclohexanecarboxyilic acid 3-phenyl-benzylamide | or a pharmaceutically acceptable salt thereof.

9. The compound according to claim 1, wherein said compound is selected from the table below

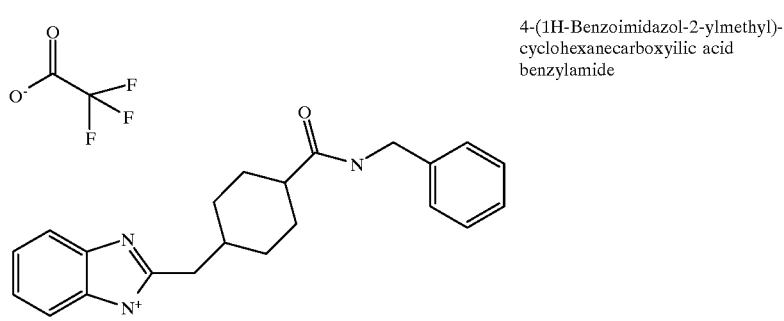
4-(1H-Benzoimidazol-2-ylmethyl)-cyclohexanecarboxyilic acid benzylamide
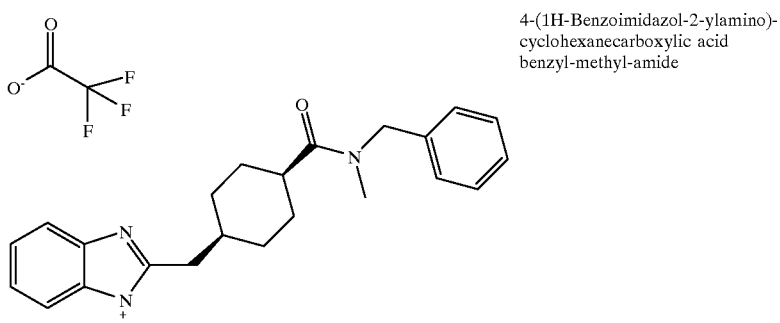
4-(1H-Benzoimidazol-2-ylamino)-cyclohexanecarboxyilic acid benzyl-methyl-amide
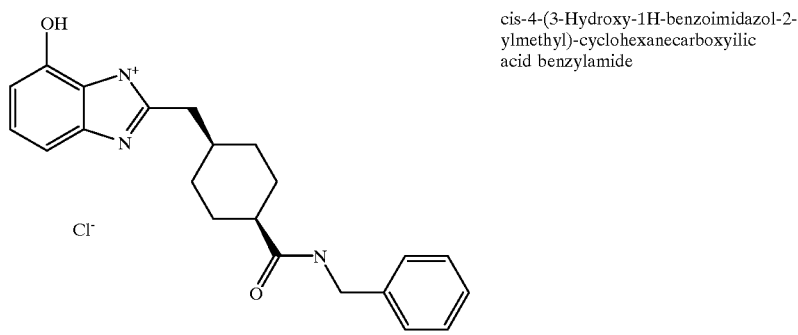
cis-4-(3-Hydroxy-1H-benzoimidazol-2-ylmethyl)-cyclohexanecarboxyilic acid benzylamide
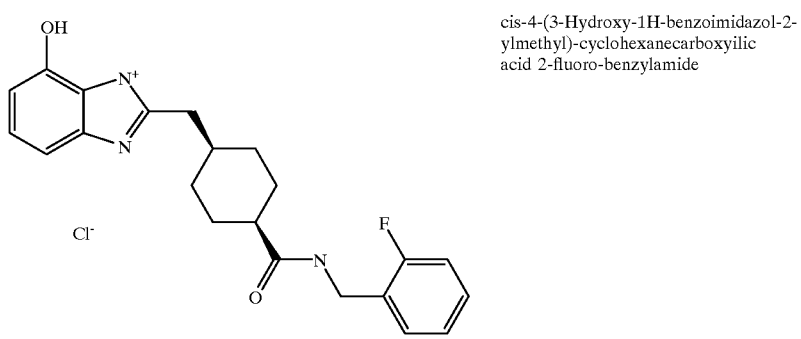
cis-4-(3-Hydroxy-1H-benzoimidazol-2-ylmethyl)-cyclohexanecarboxyilic acid 2-fluoro-benzylamide

| | -continued |
|---|---|
| 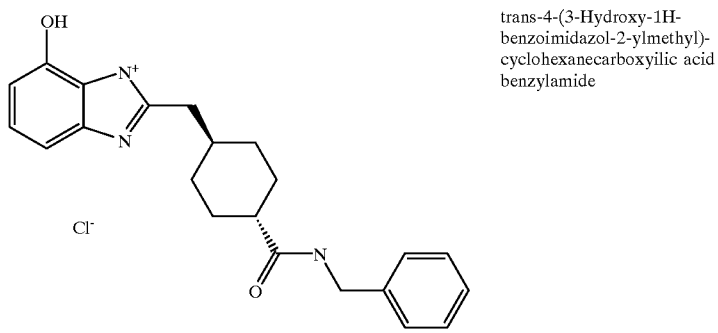 | trans-4-(3-Hydroxy-1H-benzoimidazol-2-ylmethyl)-cyclohexanecarboxyilic acid benzylamide |
| 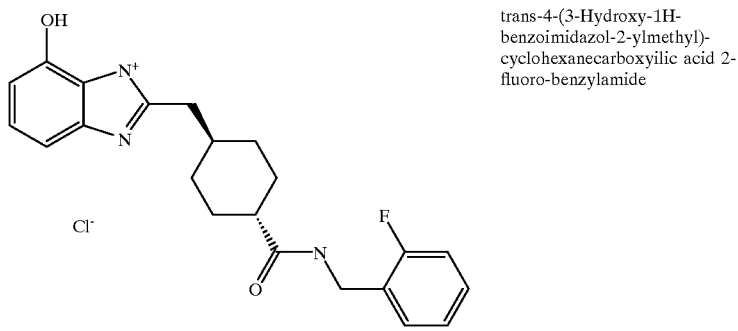 | trans-4-(3-Hydroxy-1H-benzoimidazol-2-ylmethyl)-cyclohexanecarboxyilic acid 2-fluoro-benzylamide | or a pharmaceutically acceptable salt thereof.

10. A pharmaceutical composition comprising an inert carrier and an effective amount of a compound according to claim 1.

11. A method of treating pain comprising a step of administering to one in need of such treatment an effective amount of pharmaceutical composition according to claim 10.

12. A method of treating of migraine, depression, anxiety, schizophrenia, Parkinson's disease, or stroke comprising a step of administering to one in need of such treatment an effective amount of pharmaceutical composition according to claim 10.

13. A method of treating pain comprising a step of administering to one in need of such treatment an effective amount of a compound according to claim 1.

14. A method of treating migraine, depression, anxiety, schizophrenia, Parkinson's disease, or stroke comprising a step of administering to one in need of such treatment an effective amount of a compound according to claim 1.

* * * * *